(12) United States Patent
Fujita et al.

(10) Patent No.: US 9,622,708 B2
(45) Date of Patent: Apr. 18, 2017

(54) BIOLOGICAL BODY STATE ESTIMATION DEVICE AND COMPUTER PROGRAM

(75) Inventors: Etsunori Fujita, Hiroshima (JP); Yumi Ogura, Hiroshima (JP); Yoshika Nobuhiro, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 997 days.

(21) Appl. No.: 13/881,871

(22) PCT Filed: Oct. 28, 2011

(86) PCT No.: PCT/JP2011/074962
§ 371 (c)(1),
(2), (4) Date: Apr. 29, 2013

(87) PCT Pub. No.: WO2012/057331
PCT Pub. Date: May 3, 2012

(65) Prior Publication Data
US 2013/0225940 A1    Aug. 29, 2013

(30) Foreign Application Priority Data

Oct. 29, 2010  (JP) ................. 2010-244832

(51) Int. Cl.
*A61B 5/00* (2006.01)
*A61B 5/0245* (2006.01)
(Continued)

(52) U.S. Cl.
CPC .......... *A61B 5/7235* (2013.01); *A61B 5/0205* (2013.01); *A61B 5/0245* (2013.01); *A61B 5/18* (2013.01); *A61B 5/6893* (2013.01)

(58) Field of Classification Search
CPC ... A61B 5/0295; A61B 5/0205; A61B 5/0261; A61B 5/0265; A61B 5/053;
(Continued)

(56) References Cited

U.S. PATENT DOCUMENTS

| 4,602,247 A * | 7/1986 | Seko ................ A61B 5/18 180/272 |
| 5,127,708 A * | 7/1992 | Kishi ................ A61B 5/18 297/284.1 |

(Continued)

FOREIGN PATENT DOCUMENTS

| JP | 2004 344612 | 12/2004 |
| JP | 2004 344613 | 12/2004 |

(Continued)

OTHER PUBLICATIONS

Sylvain Jasson, "Instant Power Spectrum Analysis of Heart Rate Variability During Orthostatic Tilt Using a Time/FrequencyDomain Method", Circulation. 1997;96:3521-3526 Originally published Nov. 18, 1997.*

(Continued)

*Primary Examiner* — Anhtuan T Nguyen
*Assistant Examiner* — Jae Woo
(74) *Attorney, Agent, or Firm* — Oblon, McClelland, Maier & Neustadt, L.L.P.

(57) ABSTRACT

A device to detect a state of a human being is provided. The device determines a time-series waveform of a frequency from a time-series waveform of a biological signal acquired from an upper body of a human being, and determines time-series waveforms of a frequency slope and frequency variation to analyze these frequencies. Upon analyzing the frequencies, it determines power spectrums of frequencies corresponding to a preset functional adjustment signal, fatigue reception signal, and activity adjustment signal, and then determines a state of the human being from a time-series change in each power spectrum. Dominant degrees of the functional adjustment signal and activity adjustment signal are compared as distribution rates thereof, in addition to a degree of progress of fatigue, to determine a state of the human being, for example a relaxed state, fatigued state, (Continued)

prominent state of sympathetic nervous, prominent state of parasympathetic nervous.

12 Claims, 22 Drawing Sheets

(51) Int. Cl.
*A61B 5/18* (2006.01)
*A61B 5/0205* (2006.01)

(58) Field of Classification Search
CPC ............ A61B 5/14503; A61B 5/14542; A61B 5/4836; A61B 5/4869; A61B 5/6846; A61B 5/686; A61B 5/7275; A61B 5/7282; A61B 5/18; A61B 5/0245; A61B 5/4809; A61B 5/6893; A61B 5/7235; A61B 2503/20; A61B 2503/22; A61B 5/04014; A61B 5/048; A61N 1/362; B60N 2002/4485; B60K 28/02; B60K 28/06; B60K 28/066
USPC ....... 600/301, 481, 504, 513, 519, 544, 527, 600/500, 509, 545, 372; 607/9, 25; 128/901
See application file for complete search history.

(56) References Cited

U.S. PATENT DOCUMENTS

| | | | | |
|---|---|---|---|---|
| 5,813,989 | A * | 9/1998 | Saitoh | A61B 5/18 340/576 |
| 6,097,295 | A * | 8/2000 | Griesinger | A61B 5/18 340/576 |
| 6,104,296 | A * | 8/2000 | Yasushi | A61B 5/04085 180/272 |
| 6,280,394 | B1 * | 8/2001 | Maloney | A61B 5/04888 600/546 |
| 6,293,915 | B1 * | 9/2001 | Amano | A61B 5/021 600/485 |
| 6,308,098 | B1 * | 10/2001 | Meyer | A61N 1/36521 600/547 |
| 7,183,930 | B2 * | 2/2007 | Basir | A61B 5/02455 340/521 |
| 7,529,579 | B2 * | 5/2009 | Colombo | A61B 5/02405 600/513 |
| 8,398,546 | B2 * | 3/2013 | Pacione | A61B 5/411 128/920 |
| 2003/0000522 | A1 * | 1/2003 | Lynn | A61B 5/412 128/200.24 |
| 2003/0158466 | A1 * | 8/2003 | Lynn | A61B 5/00 600/300 |
| 2004/0034285 | A1 * | 2/2004 | Sahashi | A61B 5/0245 600/300 |
| 2004/0044291 | A1 * | 3/2004 | Yasushi | A61B 5/18 600/509 |
| 2004/0046666 | A1 * | 3/2004 | Yasuchi | A61B 5/02405 340/573.1 |
| 2004/0236235 | A1 * | 11/2004 | Fujita | A61B 5/18 600/500 |
| 2004/0260440 | A1 * | 12/2004 | Fujita | G08B 21/06 701/36 |
| 2005/0042589 | A1 * | 2/2005 | Hatlestad | A61B 5/0031 434/262 |
| 2005/0075542 | A1 * | 4/2005 | Goldreich | A61B 5/0205 600/300 |
| 2005/0283205 | A1 * | 12/2005 | Lee | A61B 5/0488 607/48 |
| 2006/0106562 | A1 * | 5/2006 | Uenishi | A61B 5/18 702/113 |
| 2006/0149144 | A1 * | 7/2006 | Lynn | A61B 5/00 600/323 |
| 2006/0155175 | A1 * | 7/2006 | Ogino | A61B 5/02438 600/301 |
| 2006/0184047 | A1 * | 8/2006 | Yamashita | A61B 5/0059 600/476 |
| 2007/0078351 | A1 * | 4/2007 | Fujita | A61B 5/18 600/500 |
| 2007/0299636 | A1 * | 12/2007 | Fujita | A61B 5/1116 702/191 |
| 2008/0132383 | A1 * | 6/2008 | Einav | A61H 1/02 482/8 |
| 2009/0227883 | A1 * | 9/2009 | Zhang | A61B 5/0205 600/509 |
| 2009/0326399 | A1 * | 12/2009 | Barrero Batalloso | A61B 5/18 600/509 |
| 2012/0101395 | A1 | 4/2012 | Fujita et al. | |
| 2012/0245439 | A1 * | 9/2012 | Andre | A61B 5/0205 600/310 |
| 2013/0030256 | A1 | 1/2013 | Fujita et al. | |
| 2013/0144181 | A1 * | 6/2013 | Fogt | A61B 5/02405 600/521 |
| 2013/0150741 | A1 * | 6/2013 | Noh | A61B 5/18 600/508 |

FOREIGN PATENT DOCUMENTS

| | | |
|---|---|---|
| JP | 2006 149470 | 6/2006 |
| JP | 2007 90032 | 4/2007 |
| JP | 2009 237802 | 10/2009 |
| JP | 2011 167362 | 9/2011 |
| WO | 2005 092193 | 10/2005 |
| WO | 2010 123125 | 10/2010 |

OTHER PUBLICATIONS

Fujita, E. et al., "<Contribution>Development of the measurement method of the prediction of sleep by finger plethysmogram data," Ergonomics, vol. 41, No. 4, pp. 203 to 212, (2005) (with English abstract).

Ochiai, Y. et al., "The Application to Fatigue and Sleep Prediction, of The Signal of Biological Fluctuation Measured from Noninvasive Sensor," 39th Japan Ergonomics Society Chugoku and Shikoku Branch convention, Collection of Literatures and Papers issued on Nov. 25, 2006 from Japan Ergonomics Society Chugoku and Shikoku Branch Secretariat, Total 2 pages.

Maeda, S. et al., "Trial Manufacture of Car Seat having a Non-Aggression Biological Signal Sensing Function," 39th Japan Ergonomics Society Chugoku and Shikoku Branch Convention, Collection of Literatures and Papers issued on Nov. 25, 2006 from Japan Ergonomics Society Chugoku and Shikoku Branch Secretariat, Total 2 pages.

International Search Report Issued Dec. 27, 2011 in PCT/JP11/74962 Filed Oct. 28, 2011.

* cited by examiner peak detection method zero crossing method

Fig. 9 external force applied to blood (piston) = $\underbrace{m_p \ddot{x}}_{\text{force of reflective wave}} + \underbrace{Fg}_{\text{inertial force of blood}}$

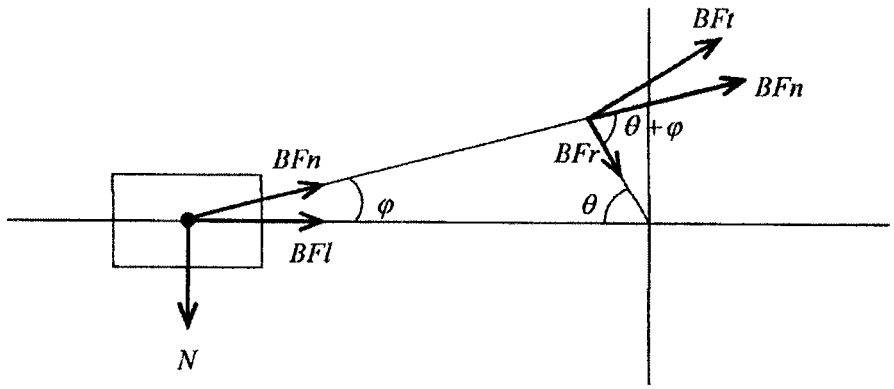

$BFl$: external force applied to blood flow
$BFn$: reaction force from backflow valve
$N$: side pressure generated by blood vessel wall
$BFt$: component force in radial direction of blood flow = rotative force of blood flow
$BFr$: component force of blood flow $BFn = BFl \sec\varphi, \quad N = BFl \tan\varphi$ $BFr = BFn \cos(\theta + \varphi) = BFl \dfrac{\cos(\theta + \varphi)}{\cos\varphi}$ $BFt = BFn \sin(\theta + \varphi) = BFl \dfrac{\sin(\theta + \varphi)}{\cos\varphi} = BFl \dfrac{\sin\theta\cos\varphi + \cos\theta\sin\varphi}{\cos\varphi}$

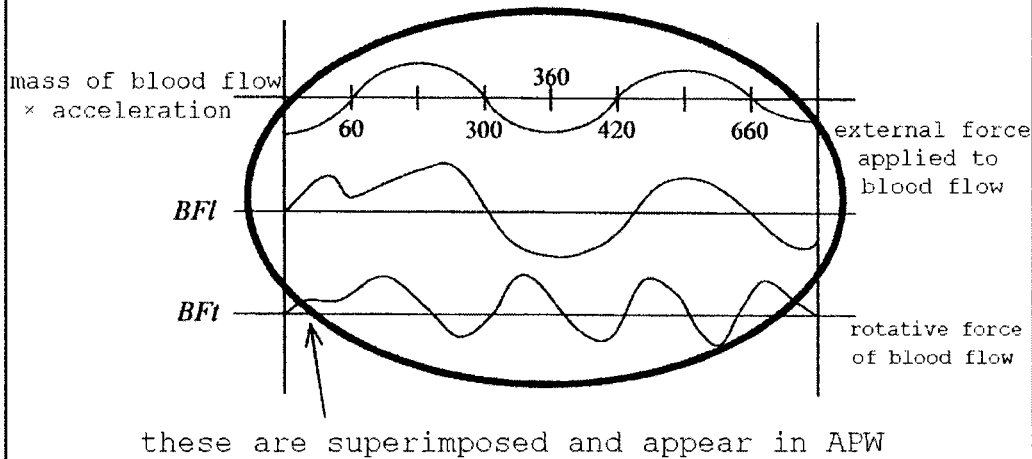

these are superimposed and appear in APW

Fig. 13
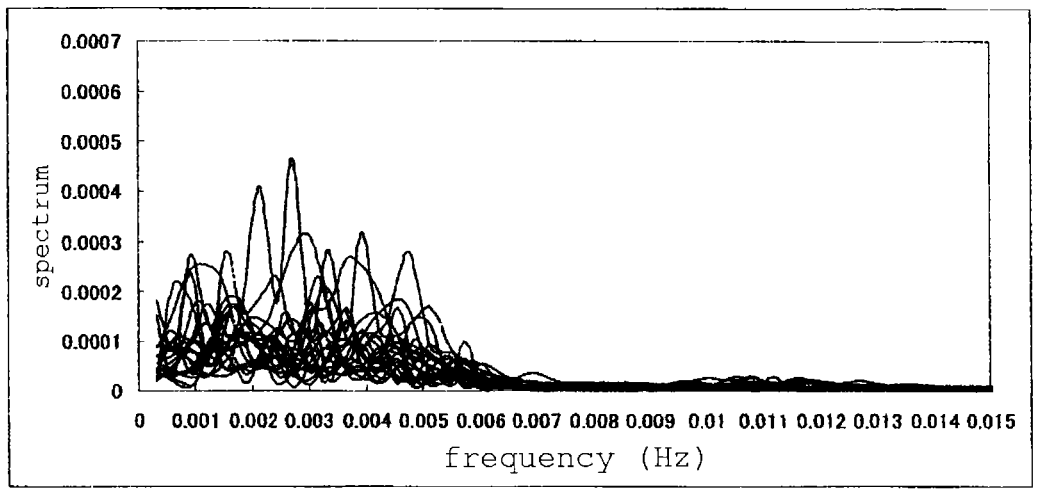
(A) spectrum of slope time-series waveform for each human subject
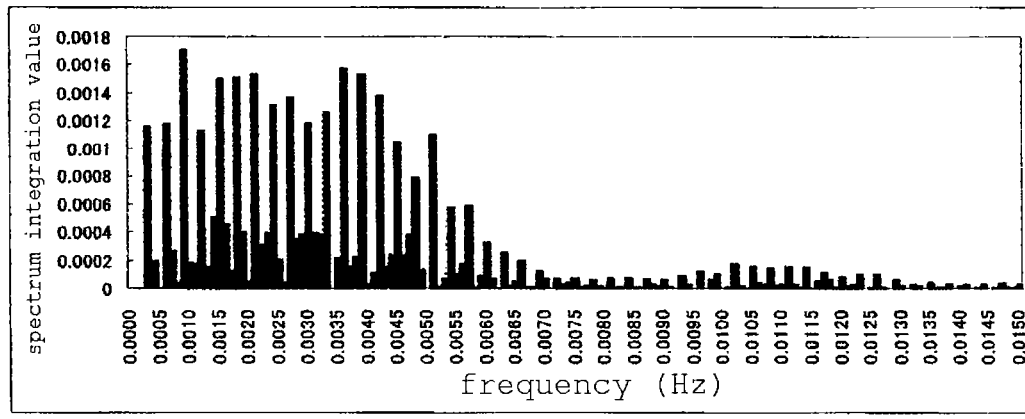
(B) integration of spectrums of (A)
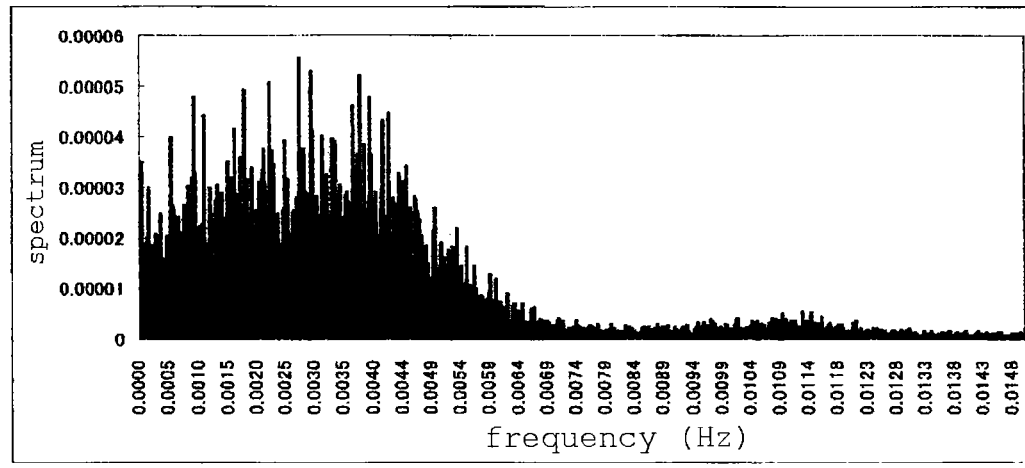
(C) frequency analysis result of merged data for 36 people in sleep introduction experiment Fig. 14
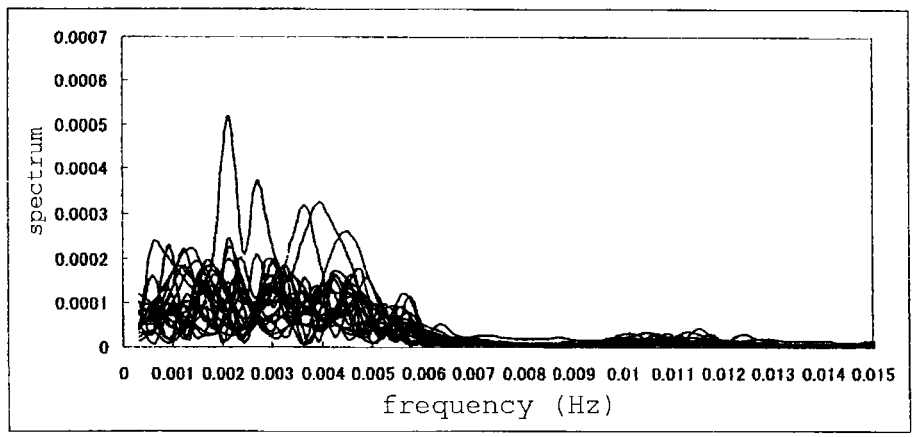
(A) spectrum of slope time-series waveform for each human subject
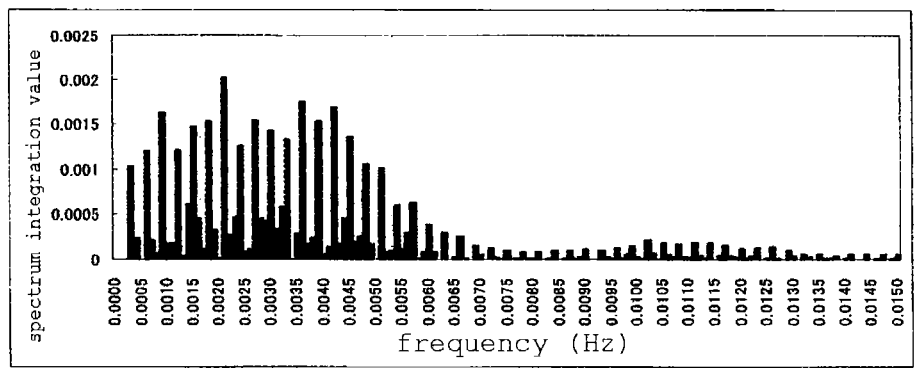
(B) integration of spectrums of (A)
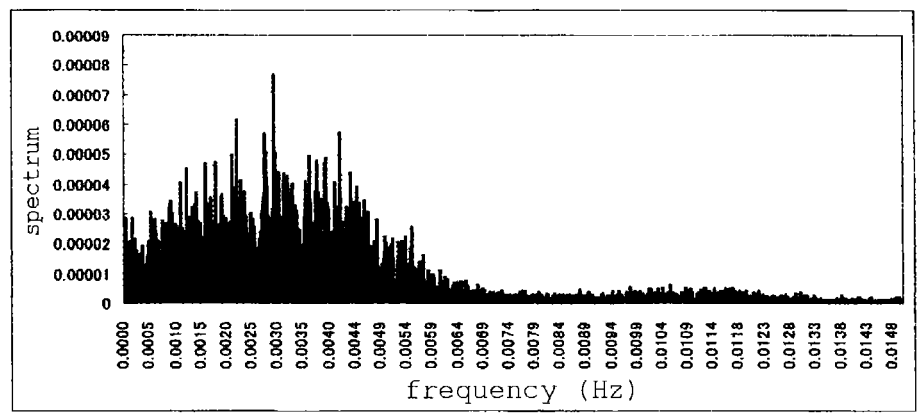
(C) frequency analysis result of merged data for 36 people in sleep introduction experiment

Fig. 15

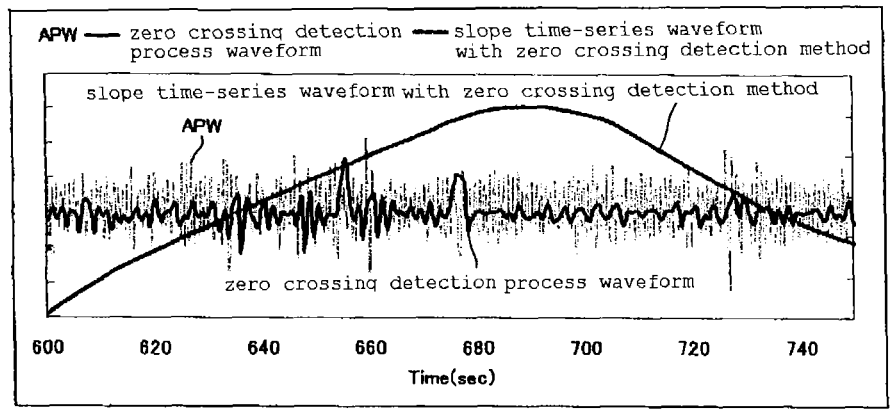

(A) comparison among APW, zero crossing detection process waveform, and slope time-series waveform with zero crossing detection method

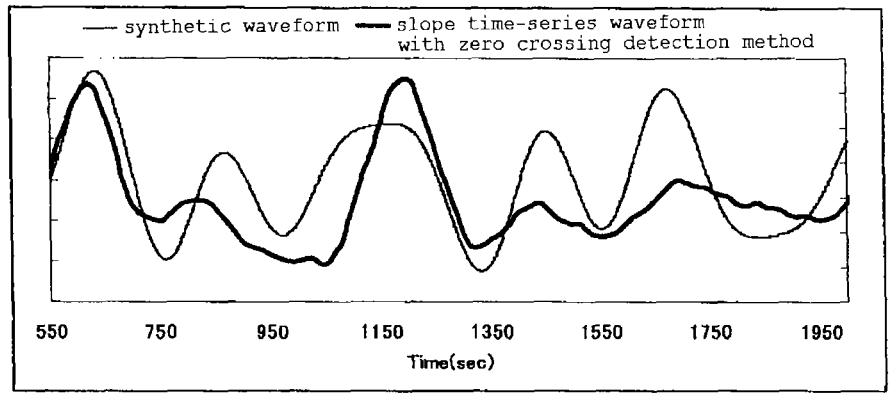

(B) comparison between synthetic waveform (0.0017 Hz, 0.0035 Hz and 0.0053 Hz) and slope time-series waveform with zero crossing detection method

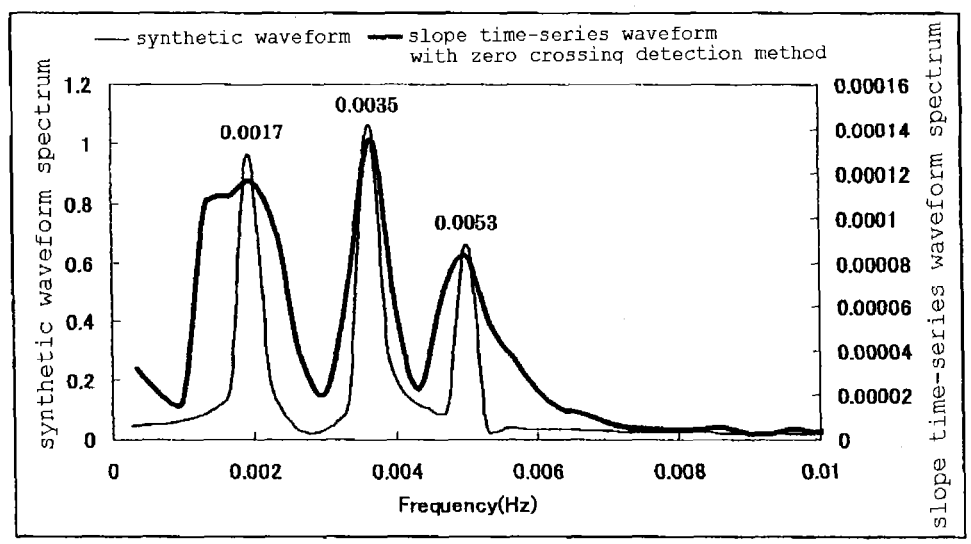

(C) comparison of frequency analysis result between synthetic waveform (0.0017 Hz, 0.0035 Hz and 0.0053 Hz) and slope time-series waveform with zero crossing detection method

Fig. 16

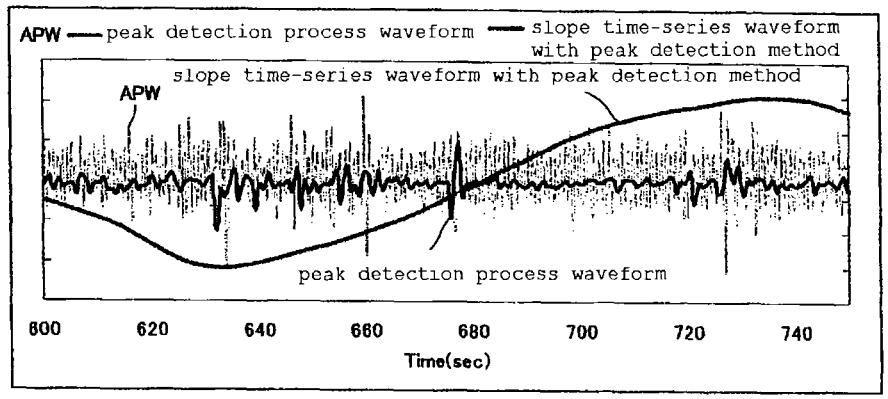

(A) comparison among APW, peak detection process waveform, and slope time-series waveform with peak detection method

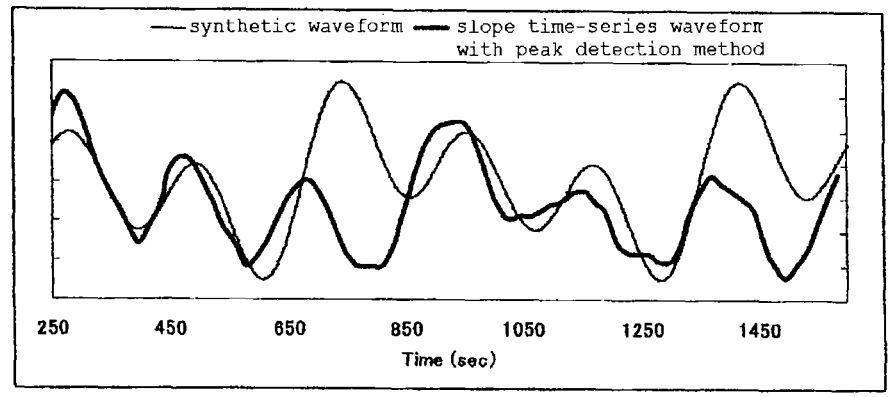

(B) comparison between synthetic waveform (0.0017 Hz, 0.0035 Hz and 0.0053 Hz) and slope time-series waveform with peak detection method

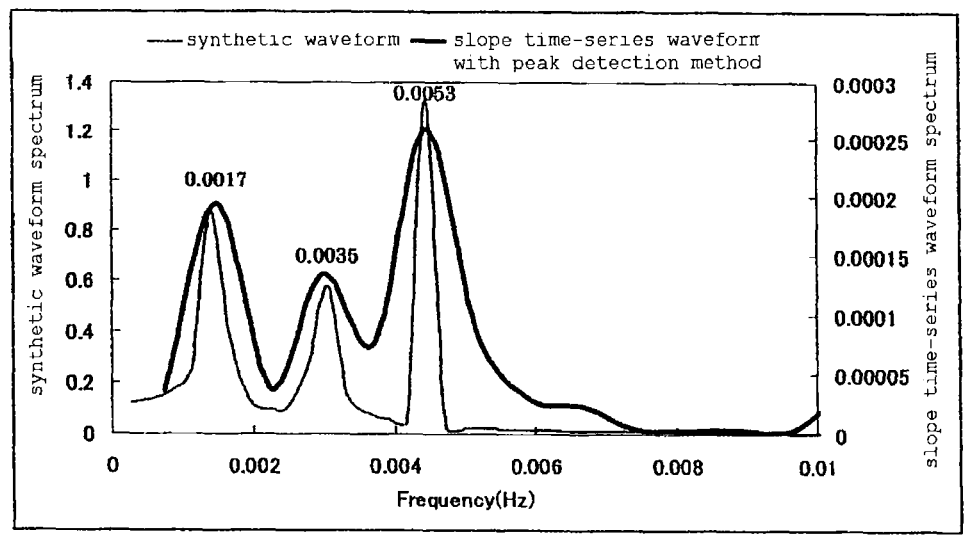

(C) comparison of frequency analysis result between synthetic waveform (0.0017 Hz, 0.0035 Hz and 0.0053 Hz) and slope time-series waveform with peak detection method

Fig. 20

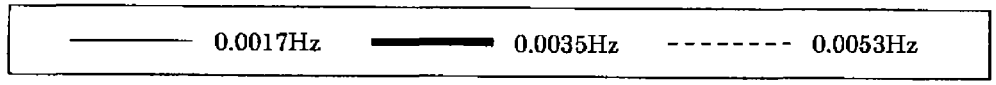

■determination result of slope new distribution rates of frequencies with 0x detection method and peak detection method (sleep experiment)

| | APW⊕ determination ||||
|---|---|---|---|---|
| | weak sleepiness (APW①) | strong sleepiness (APW②) | resisting sleepiness (APW③) | prediction of falling asleep (APW④) |
| slope of frequency 0x detection method | | | | |
| slope of frequency peak detection method | | | | |
| psychological determination — dozing/sleepiness | 9 | 8 | 3 | 14 |
| psychological determination — awake | 0 | 1 | 1 | 4 |
| psychological determination — falling asleep | 6 | 3 | 5 | 0 |
| example of falling asleep — example of falling asleep in 20 min | 4 | 5 | 2 | 9 |
| example of falling asleep — example of falling asleep after 20 min | 1 | 1 | 0 | 4 |
| proportion of falling asleep after determination | 5/9 | 6/9 | 2/4 | 13/18 |
| | 55.6% | 66.7% | 50% | 72.2% |

Fig. 21

■determination result of slope new distribution rates of frequencies with 0x detection method by using basic line (awakening experiment)

| slope of frequency<br>0x detection method | APW⊖ determination | | |
|---|---|---|---|
| | ╱ | ─ | ╲ |
| psycholog-ical determina-tion awake | 5 | 14 | 1 |
| weak sleepiness | 1 | 3 | 4 |

Fig. 22

| | Awake | Sleep |
|---|---|---|
| APW⊖determination | 20 | 8 |
| APW⊕determination | 6 | 48 |

|  | fall asleep | not fall asleep |
|---|---|---|
| APW⊖ (awake state) | 0 | 28 |
| APW①②③ (state where sleepiness emerges) | 13 | 23 |
| APW④ (predictive phenomenon of sleepiness emerges) | 13 | 5 |

Fig. 26 A

| | | APW/zero crossing detection method | |
|---|---|---|---|
| | | range from 30% to 100% relative to sleeping state at 0.25Hz | over 100% relative to sleeping state at 0.25Hz |
| biological body state | transition state | 5 | 1 |
| | usual state | 4 | 10 |

Fig. 26 B

| | | APW/peak detection method | |
|---|---|---|---|
| | | range from 30% to 100% relative to sleeping state at 0.25Hz | over 100% relative to sleeping state at 0.25Hz |
| biological body state | transition state | 4 | 6 |
| | usual state | 8 | 8 |

BIOLOGICAL BODY STATE ESTIMATION DEVICE AND COMPUTER PROGRAM

TECHNICAL FIELD

The present invention relates to a technique for estimating a state of a biological body using a time-series waveform of a biological signal obtained from an upper body of a person.

BACKGROUND ART

Monitoring a biological body state of a driver during driving has attracted attention as a preventive measure against an accident or the like in recent years. The present applicant discloses techniques of disposing a pressure sensor in a seat cushion section, obtaining and analyzing breech pulse waves, and determining a sleep prediction phenomenon in Patent Literatures 1 to 3.

Specifically, a maximum value and a minimum value of a time-series waveform of a pulse wave are obtained by a smoothing differentiation method of Savitzky and Golay, respectively. The maximum value and the minimum value are obtained for each 5 seconds so that their mean values are obtained. Using a square of a difference between the respective mean values of the maximum values and the minimum values obtained as a power value, the power value is plotted for each 5 seconds so that a time-series waveform of the power value is produced. In order to read a global change of the power value from this time-series waveform, a slope of the power value regarding a certain time window Tw (180 seconds) is obtained by least-square method. Next, the slope regarding the next time window Tw is similarly calculated in an overlapped time TI (162 seconds) and the calculation results are plotted. A time-series waveform of the slope of the power value is obtained by repeating this calculation (movement calculation) sequentially. On the other hand, the maximum Lyapunov exponent is obtained by applying Chaos analysis to the time-series waveform of the pulse wave, a maximum value is obtained by a smoothing differentiation like the above, and a time-series waveform of a slope of the maximum Lyapunov exponent is obtained by conducting movement calculation.

Then, the time-series waveform of the slope of the power value and the time-series waveform of the slope of the maximum Lyapunov exponent take phases opposite to each other, and a waveform having a large amplitude at a low frequency in the time-series waveform of the slope of the power value is determined as a characteristic signal indicating a sleep prediction and a point at which the amplitude has become small thereafter is determined as a sleep-onset point.

Further, as Patent Literature 4, a system provided with an airbag (air pack) including a three-dimensional solid fabric inserted therein, where the air pack is disposed at a site corresponding to a waist portion of a person, an air pressure fluctuation in the air pack is measured, a biological signal of the person is detected from the time-series waveform of the air pressure fluctuation obtained, and the biological body state of the person is analyzed is disclosed. Further, in Non-Patent Literatures 1 and 2, trials for detecting a biological signal of a person by disposing an air pack sensor along a lumber iliocostal muscle are reported. This air pressure fluctuation of the air pack is caused by fluctuation in a downward aorta with movement of a heart, and a state change closer to the movement of the heart than use of the breech pulse waves in Patent Literatures 1 and 2 can be captured.

PRIOR ART LITERATURES

Patent Literature

Patent Literature 1: Japanese Patent Application Laid-Open No. 2004-344612
Patent Literature 2: Japanese Patent Application Laid-Open No. 2004-344613
Patent Literature 3: WO2005/092193A1
Patent Literature 4: Japanese Patent Application Laid-Open No. 2007-90032

Non-Patent Literatures

Non-Patent Literature 1: "ORIGINAL: DEVELOPMENT OF THE MEASUREMENT METHOD OF THE PREDICTION OF SLEEP BY FINGER PLETHYSMOGRAM DATA" by Etsunori FUJITA (and eight others), Ergonomics, Vol 41, No. 4 ('05)
Non-Patent Literature 2: "APPLICATION OF BIOLOGICAL WANDERING SIGNAL MEASURED BY NON-INVASIVE TYPE SENSOR TO FATIGUE AND SLEEP PREDICTION" by Naoki OCHIAI (and six others), 39th Japan Ergonomics Society Chugoku and Shikoku Branch convention, Collection of Literatures and Papers issued on Nov. 25, 2006 from Japan Ergonomics Society Chugoku and Shikoku Branch Secretariat
Non-Patent Literature 3: "TRIAL PRODUCTION OF VEHICLE SEAT HAVING NON-INVASIVE BIOLOGICAL SIGNAL SENSING FUNCTION" by Shinichiro MAEDA (and four others), 39th Japan Ergonomics Society Chugoku and Shikoku Branch Convention, Collection of Literatures and Papers issued on Nov. 25, 2006 from Japan Ergonomics Society Chugoku and Shikoku Branch Secretariat

SUMMARY OF INVENTION

Technical Problem

As described above, in the techniques described in Patent Literatures 1 to 4 and Non-Patent Literatures 1 to 3, the time where the time-series waveform of the slope of the power value and the time-series waveform of the slope of the maximum Lyapunov exponent has taken phases opposite to each other and a waveform having a large amplitude at a low frequency has occurred in the time-series waveform of the slope of the power value is regarded as the sleep prediction phenomenon.

Moreover, the applicant has proposed the following technique as Japanese Patent Application Laid-Open No. 2009-237802. That is, it is a technique in which a time-series waveform of a frequency is acquired from the time-series waveform of a biological signal obtained by biological signal measuring means, and a frequency slope time-series waveform and a frequency fluctuation time-series waveform acquired from this time-series waveform of the frequency are used so as to determine a state of a human being by combining signs of the frequency slope time-series waveform, the signs of an integral waveform of the frequency slope time-series waveform, emergence of an opposite phase (the emergence of the opposite phase indicates a sleep prediction) when the frequency slope time-series waveform and the frequency fluctuation time-series waveform are outputted in superposition and the like.

The applicant has proposed the technique for grasping a state of a human being by using a biological signal as described above; however a proposal of a technique for grasping a state of a human being more precisely has been constantly in demand. Moreover, if multiple methods for grasping a state of a human being are present, a state of a human being can be grasped more precisely by using these methods in combination. The present invention has been made in view of the above, and aims to provide a technique for analyzing a biological signal by using a new analysis method and for grasping a state of a human being.

Solution to Problem

Here, in atrial fibrillation that is one of heart diseases, it is said that a characteristic of a cardiovascular fluctuation is switched at 0.0033 Hz, and fluctuations for adjusting the fluctuation of 0.0033 Hz are present in the vicinity of and lower than 0.0033 Hz. As a result of determining a frequency slope time-series waveform that calculates a low-frequency fluctuation present in a biological signal and analyzing a frequency thereof, it is confirmed that fluctuations centered at 0.0017 Hz and 0.0035 Hz, which are lower than 0.0033 Hz and in the vicinity of 0.0033 Hz, respectively, are generated. Also, in addition to the two fluctuations, it is confirmed that a fluctuation centered at 0.0053 Hz is generated.

Thus, from these findings, the inventor sets a signal of 0.0035 Hz (hereinafter referred to as a "fatigue reception signal") as a basis, and uses it as a signal indicating a degree of progress of fatigue in a usual active state; uses a signal of 0.0053 Hz (hereinafter referred to as an "activity adjustment signal") as a signal in which a degree of influence exerted by the control of a brain and an autonomic nerve system emerges during an activity; and uses a signal of 0.0017 Hz (hereinafter referred to as a "functional adjustment signal"), which is lower than 0.0033 Hz, as a signal controlling the disorder or functional deterioration of a body. By paying attention to the determination of a state of a human being from time-series changes in power spectrums of these signals, the inventor has reached the completion of the present invention.

Moreover, as a biological signal, the applicant pays attention not to a digital volume pulse but to grasping of a degree of fluctuation of atrium and aorta. That is because a wall of an aorta is rich in elasticity among arteries and can receive a high pressure of blood directly pumped out of a heart and also, there is an aortic valve as a valve for preventing backflow immediately out of the left ventricle of the heart. Thus, by analyzing a biological signal grasping a degree of fluctuation of the atrium and aorta, an adjustment ring of a negative feedback mechanism of the brain and the autonomic nerve system for homeostasis of a biological body can be well grasped, whereby not only the activity of the autonomic nerve but also an activation state of a brain function can be grasped, and a biological body state can be estimated more accurately.

Specifically, a biological body state estimation device according to the present invention acquires a biological signal from an upper body of the human being, and estimates a state of a human being by using the biological signal. The biological body state estimation device includes: frequency calculating means for determining a time-series waveform of a frequency from a time-series waveform of the biological signal acquired by the biological signal measuring means; frequency slope time-series analysis calculating means for subjecting the time-series waveform of the frequency of the biological signal acquired by the frequency calculating means to movement calculation for determining a slope of the frequency at each predetermined time window set with a predetermined overlap time, and for outputting a time-series change in the slope of the frequency acquired at each time window as a frequency slope time-series waveform; spectrum time-series change calculating means for analyzing a frequency of the frequency slope time-series waveform acquired by the frequency slope time-series analysis calculating means, and for determining a time-series change in a power spectrum; distribution rate waveform calculating means for extracting frequency components corresponding to a preset functional adjustment signal, fatigue reception signal and activity adjustment signal from the time-series change in the power spectrum acquired by the spectrum time-series change calculating means, for calculating proportions of the three frequency components in time sequence when a sum of power spectrums of the three frequency components is set to 100, and for determining the proportions as distribution rate waveforms; and determining means for locating a waveform change pattern of the three frequency components in the distribution rate waveforms acquired by the distribution rate waveform calculating means, and for determining a state of a human being by comparing the located waveform change pattern with correlative data between a waveform change pattern and a state of a human being which the correlative data is stored in a storage unit in advance.

It is preferable that: the frequency calculating means includes first frequency calculating means for pinpointing a zero-crossing point in the time-series waveform of the biological signal obtained by the biological signal measuring means, and for determining the time-series waveform of the frequency of the biological signal by using this zero-crossing point, the zero-crossing point being a point at which a positive of the time-series waveform is switched to a negative; the frequency slope time-series calculating means includes first frequency slope time-series analysis calculating means for subjecting the time-series waveform of the frequency of the biological signal which is acquired by the first frequency calculating means to the movement calculation for determining the slope of the frequency at each predetermined time window set with the predetermined overlap time, and for outputting the time-series change in the slope of the frequency acquired at each time window as the frequency slope time-series waveform; and the spectrum time-series change calculating means is configured to analyzes the frequency of the frequency slope time-series waveform acquired by the first frequency slope time-series analysis calculating means, and to determine the time-series change in the power spectrum.

It is preferable that: the frequency calculating means includes second frequency calculating means for determining a maximum value of the time-series waveform of the biological signal obtained from the biological signal measuring means by smoothing and differentiating the time-series waveform, and determining the time-series waveform of the frequency of the biological signal by using this maximum value; the frequency slope time-series calculating means includes second frequency slope time-series analysis calculating means for subjecting the time-series waveform of the frequency of the biological signal which is acquired by the second frequency calculating means to the movement calculation for determining the slope of the frequency at each predetermined time window set with the predetermined overlap time, and for outputting the time-series change in the slope of the frequency acquired at each time window as the frequency slope time-series waveform; and the spectrum time-series change calculating means is configured to analyze the frequency of the frequency slope time-series waveform acquired by the second frequency slope time-series analysis calculating means, and to determine the time-series change in the power spectrum.

It is preferable that the determining means is configured to determine a time zone in which the functional adjustment signal and the fatigue reception signal are opposite in phase to be a period during which a sleepiness-related phenomenon emerges, as the waveform change pattern of the distribution rate waveform. It is preferable that the determining means is configured to determine a time zone in which the functional adjustment signal and the fatigue reception signal are opposite in phase and the distribution rate of the activity adjustment signal is equal to or higher than a predetermined distribution rate to be a period during which a predictive phenomenon of falling asleep emerges, as the waveform change pattern of the distribution rate waveform. It is preferable that for use in the distribution rate waveform calculating means, a frequency of the functional adjustment signal is 0.0017 Hz, a frequency of the fatigue reception signal is 0.0035 Hz, and a frequency of the activity adjustment signal is 0.0053 Hz.

A computer program according to the present invention is to be set in a biological body state estimation device to acquire a biological signal from an upper body of the human being and to estimate a state of a human being by using the biological signal. The computer program causing a computer to perform: a frequency calculating step of determining a time-series waveform of a frequency from a time-series waveform of the biological signal acquired by the biological signal measuring means; a frequency slope time-series analysis calculating step of subjecting the time-series waveform of the frequency of the biological signal acquired in the frequency calculating step to movement calculation for determining a slope of the frequency at each predetermined time window set with a predetermined overlap time, and of outputting a time-series change in the slope of the frequency acquired at each time window as a frequency slope time-series waveform; a spectrum time-series change calculation step of analyzing a frequency of the frequency slope time-series waveform acquired in the frequency slope time-series analysis calculating step, and of determining a time-series change in a power spectrum; a distribution rate waveform calculation step of extracting frequency components corresponding to a preset functional adjustment signal, fatigue reception signal and activity adjustment signal from the time-series change in the power spectrum acquired in the spectrum time-series change calculating step, of calculating proportions of the three frequency components in time sequence when a sum of power spectrums of the three frequency components is set to 100, and of determining the proportions as distribution rate waveforms; and a determining step of locating a waveform change pattern of the three frequency components in the distribution rate waveforms acquired in the distribution rate waveform calculating step, and of determining a state of a human being by comparing the located waveform change pattern with correlative data between a waveform change pattern and a state of a human being which the correlative data is stored in a storage unit in advance.

It is preferable that: the frequency calculating step includes a first frequency calculation step of pinpointing a zero-crossing point in the time-series waveform of the biological signal obtained by the biological signal measuring means, and for determining the time-series waveform of the frequency of the biological signal by using this zero-crossing point, the zero-crossing point being a point at which a positive of the time-series waveform is switched to a negative; the frequency slope time-series calculating step includes a first frequency slope time-series analysis calculation step of subjecting the time-series waveform of the frequency of the biological signal which is acquired in the first frequency calculating step to the movement calculation for determining the slope of the frequency at each predetermined time window set with the predetermined overlap time, and of outputting the time-series change in the slope of the frequency acquired at each time window as the frequency slope time-series waveform; and the spectrum time-series change calculation step is configured to analyze the frequency of the frequency slope time-series waveform acquired in the first frequency slope time-series analysis calculating step, and to determine the time-series change in the power spectrum.

It is preferable that: the frequency calculating step includes a second frequency calculation step of determining a maximum value of the time-series waveform of the biological signal obtained from the biological signal measuring means by smoothing and differentiating the time-series waveform, and determining the time-series waveform of the frequency of the biological signal by using this maximum value; the frequency slope time-series calculating step includes a second frequency slope time-series calculating step of subjecting the time-series waveform of the frequency of the biological signal which is acquired in the second frequency calculating step to the movement calculation for determining the slope of the frequency at each predetermined time window set with the predetermined overlap time, and of outputting the time-series change in the slope of the frequency acquired at each time window as the frequency slope time-series waveform; and the spectrum time-series change calculation step is configured to analyze the frequency of the frequency slope time-series waveform acquired in the second frequency slope time-series analysis calculating step, and to determine the time-series change in the power spectrum.

It is preferable that the determining step is configured to determine a time zone in which the functional adjustment signal and the fatigue reception signal are opposite in phase to be a period during which a sleepiness-related phenomenon emerges, as the waveform change pattern of the distribution rate waveform. It is preferable that the determining step is configured to determine a time zone in which the functional adjustment signal and the fatigue reception signal are opposite in phase and the distribution rate of the activity adjustment signal is equal to or higher than a predetermined distribution rate to be a period during which a predictive phenomenon of falling asleep emerges, as the waveform change pattern of the distribution rate waveform. It is preferable that for use in the distribution rate waveform calculating step, a frequency of the functional adjustment signal is 0.0017 Hz, a frequency of the fatigue reception signal is 0.0035 Hz, and a frequency of the activity adjustment signal be 0.0053 Hz.

Advantageous Effect of Invention

The present invention has means for determining a time-series waveform of a frequency from a time-series waveform of a biological signal acquired from an upper body of a human being, and further for determining a time-series waveform of a frequency slope to analyze a frequency. More preferably, the present invention has means for determining a time-series waveform of a frequency variation to analyze a frequency. Upon analyzing the frequency, it determines power spectrums of frequencies corresponding to a preset functional adjustment signal, fatigue reception signal, and activity adjustment signal. Then, it determines a state of a human being from a time-series change in each power spectrum. Since the fatigue reception signal indicates the degree of progress of fatigue in a usual active state, the dominant degrees of the functional adjustment signal and the activity adjustment signal are compared as distribution rates thereof, in addition to the degree of progress of fatigue, thereby being able to determine a state of a human being (a relaxed state, a fatigued state, a prominent state of the sympathetic nervous, a prominent state of the parasympathetic nervous, and the like) more precisely.

BRIEF DESCRIPTION OF THE DRAWINGS

FIG. 9 is a diagram showing a method of determining a force generated in an aortic, with regard to the heart model likened to the piston and crank mechanism

FIGS. 13A to C are diagrams showing analysis results of a slope time-series waveform of a frequency to which the zero-crossing method (0x detection method) is applied and which is obtained from first frequency slope time-series analysis calculating means.

FIGS. 14A to C are diagrams showing analysis results of a slope time-series waveform of a frequency to which the peak detection method is applied and which is obtained from second frequency slope time-series analysis calculating means.

FIG. 15A shows a comparison among an APW, a waveform obtained by subjecting the APW to the zero crossing detection process, and a slope time-series waveform produced by the zero crossing detection method; FIG. 15B shows a comparison between a synthetic waveform of sinusoidal waves of 0.0017 Hz, 0.0035 Hz and 0.0053 Hz and the slope time-series waveform produced by the zero crossing detection method; and FIG. 15C shows a comparison of a frequency analysis result between the synthetic waveform and the slope time-series waveform produced by the zero crossing detection method.

FIG. 16A shows a comparison between among an APW, a waveform obtained by subjecting the APW to the peak detection process, and a slope time-series waveform produced by the peak detection method; FIG. 16B shows a comparison between a synthetic waveform of sinusoidal waves of 0.0017 Hz, 0.0035 Hz and 0.0053 Hz and the slope time-series waveform produced by the peak detection method; and FIG. 16C shows a comparison of a frequency analysis result between the synthetic waveform and the slope time-series waveform produced by the peak detection method.

FIG. 20 is a diagram showing waveforms of distribution rates of the above three frequency components in a heart-part oscillation wave as to a human subject for a representative example in the sleep introduction experiment.

FIG. 21 shows patterns of a slope time-series waveform produced by the zero-crossing method, in an awake state.

FIG. 22 is a diagram showing a correlation between results of FIGS. 20 and 21 and a state of a human being.

FIGS. 26A and B are diagrams for explaining a method of determining a state of a human being by analyzing frequencies of waveforms produced by applying the zero crossing and peak detection methods to the APW of FIG. 25.

DESCRIPTION OF EMBODIMENTS

Figure 1:
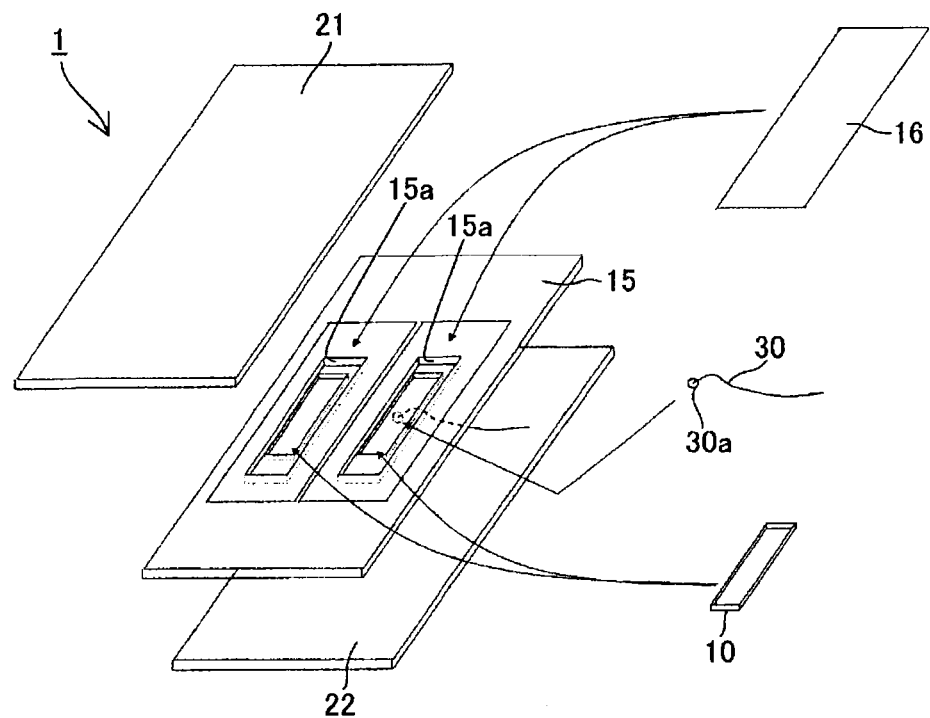
FIG. 1 is a diagram showing biological signal measuring means used in an embodiment of the present invention.
Figure 2:
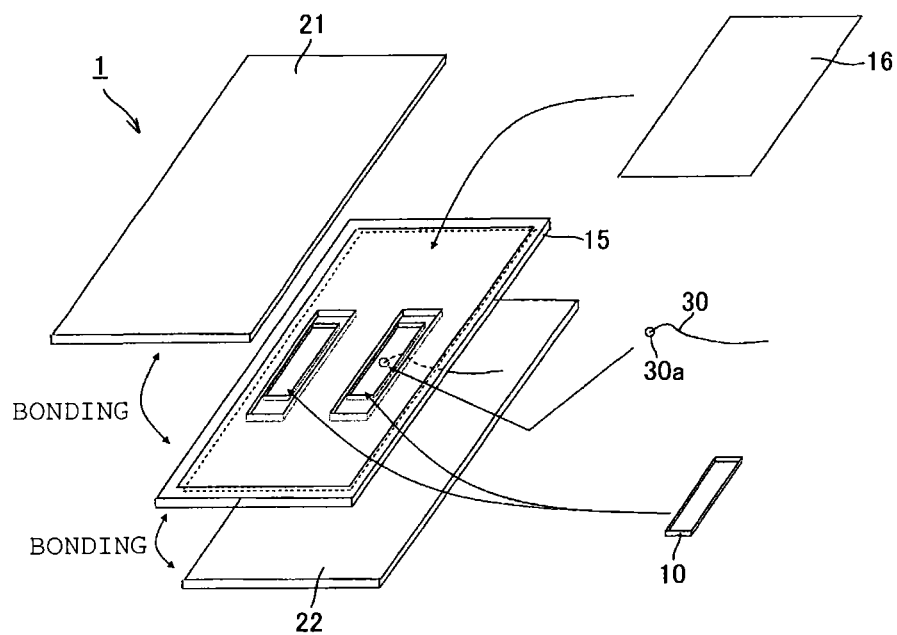
FIG. 2 is a diagram showing another form of the biological signal measuring means according to the above-described embodiment.
Figure 3:
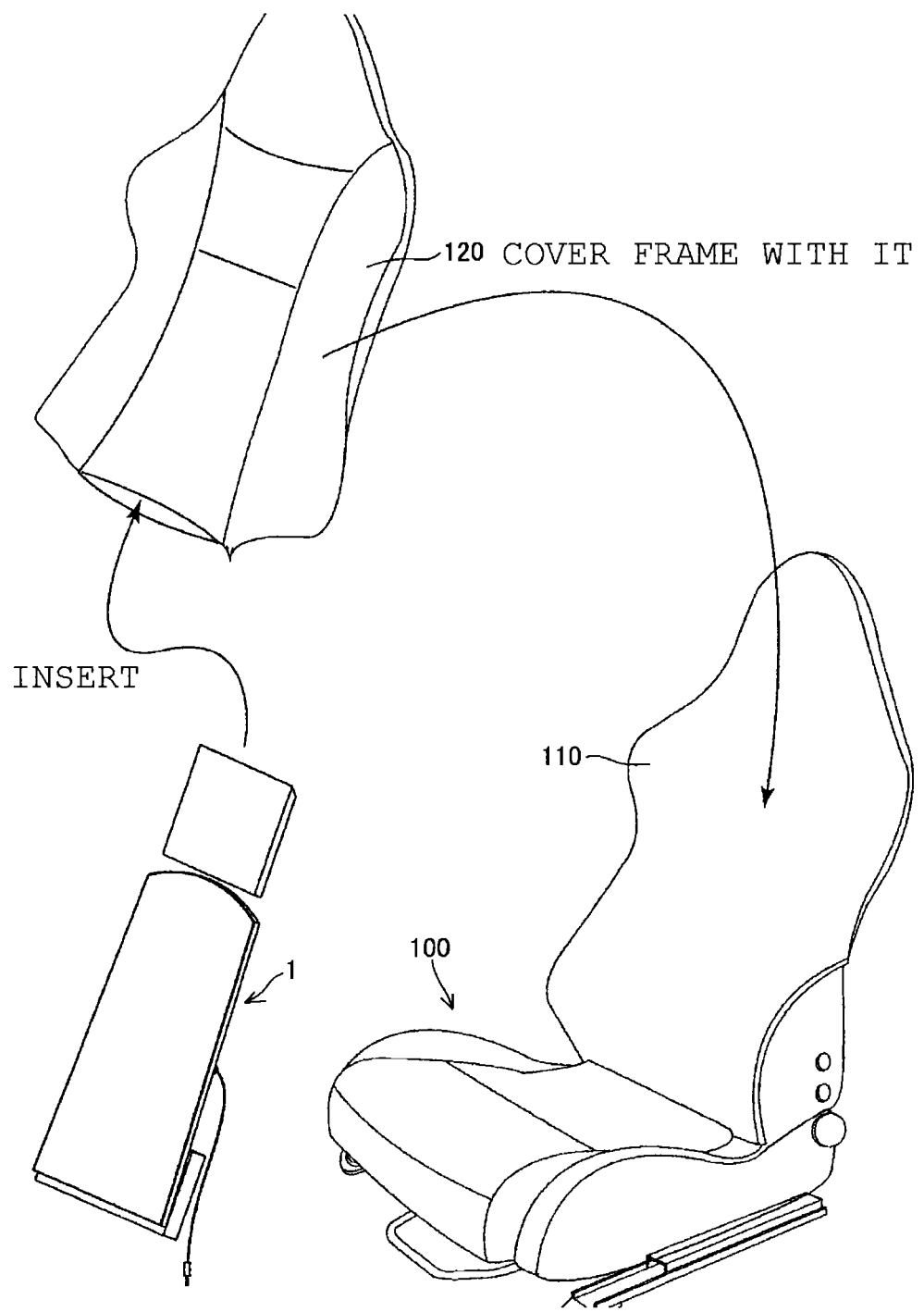
FIG. 3 is a diagram showing a process of incorporating the above-described biological signal measuring means in a seat.

The present invention will be described below in further detail on the basis of an embodiment of the present invention shown in the drawings. FIGS. 1 and 2 are diagrams showing biological signal measuring means 1 which acquires a biological signal, or a heart portion swinging wave in this case (a biological signal involved by the motion of an atrium and the fluctuation of an aorta which is detected at the back portion of the upper body of a human being), which is a subject to be analyzed by a biological body state estimation device 60 according to this embodiment, and FIG. 3 is a diagram showing a process of incorporating the biological signal measuring means 1 in a seat 100 for a vehicle. First, this biological signal measuring means 1 will be described. The biological signal measuring means 1 includes a three-dimensional knitted material 10, a three-dimensional knitted material supporting member 15, a film 16, a plate-shaped foam bodies 21 and 22, and a vibration sensor 30.

The three-dimensional knitted material 10 is, as disclosed in Japanese Unexamined Patent Application Publication No. 2002-331603, for example, a knitted fabric having a three-dimensional structure having a pair of ground knitted fabrics arranged separately from each other and a large number of connecting fibers reciprocating between the pair of ground knitted fabrics and connecting the both.

One of the ground knitted fabrics is formed of a flat knitted fabric composition (fine stitch) which is continuous both in a wale direction and a coarse direction from a yarn obtained by twisting a monofilament, for example, while the other ground knitted fabric is formed having a knitted structure having a honeycomb-shaped (hexagonal) mesh from a yarn obtained by twisting a short fiber, for example. It is needless to say that the knitted fabric composition is optional and its combination is also optional such that a knitted fabric composition other than the fine-stitch composition or the honeycomb-shape can be employed, alternatively, the fine-stitch composition can be employed for the both. The connecting fiber is knitted between the two ground knitted fabrics so that the one ground knitted fabric and the other ground knitted fabric maintain a predetermined interval. In this embodiment, since the solid vibration of the three-dimensional knitted material or particularly the string vibration of the connecting fiber is to be detected, the connecting fiber is preferably formed of a monofilament, but the connecting fiber may also be formed of a multifilament in order to adjust a resonance frequency in accordance with the type of a biological signal to be extracted.

Moreover, it is preferable that the three-dimensional knitted material 10 have a spring constant, such that its load-deflection characteristic in a thickness direction becomes approximate to the load-deflection characteristic of a muscle in the buttocks of a human being, within a range up to the load of 100 N when the three-dimensional knitted material 10 is placed on a measuring plate and pressurized by a pressure plate having a diameter of 30 mm or a diameter of 98 mm. Specifically, it is preferable to use the material having the spring constant within a range of 0.1 to 5 N/mm when being pressurized by a pressure plate having a diameter of 30 mm or the material having a spring constant within a range of 1 to 10 N/mm when being pressurized by a pressure plate having a diameter of 98 mm. Because of approximation to the load-deflection characteristic of the muscle in the buttocks of a human being, the three-dimensional knitted material is balanced with the muscle, and when a biological signal of heart rate, respiration, atrial and aortic oscillations and the like is propagated, the three-dimensional knitted material generates the vibration similar to that in the human muscle, and the biological signal can be propagated without large attenuation.

As such three-dimensional knitted material, the following may be used, for example. Each of the three-dimensional knitted materials can be used by being stacked in plural as necessary.

(1) Product number: 49076D (by Suminoe Textile Co., Ltd.) Material:
Ground knitted fabric on the front side: Twisted yarn of polyethylene terephthalate fiber false twisted yarn of 300 decitex/288f and polyethylene terephthalate fiber false twisted yarn of 700 decitex/192f
Ground knitted fabric on the back side: Combination of polyethylene terephthalate fiber false twisted yarn of 450 decitex/108f and polytrimethylene terephthalate monofilament of 350 decitex/1f
Connecting fiber: polytrimethylene terephthalate monofilament of 350 decitex/1f (2) Product number: 49011D (by Suminoe Textile Co., Ltd.) Material:
Ground knitted fabric (warp): Polyethylene terephthalate fiber false twisted yarn of 600 decitex/192f
Ground knitted fabric (weft): Polyethylene terephthalate fiber false twisted yarn of 300 decitex/72f
Connecting fiber: polyethylene terephthalate monofilament of 800 decitex/1f (3) Product number: 49013D (by Suminoe Textile Co., Ltd.) Material:
Ground knitted fabric on the front side: Two twisted yarns of polyethylene terephthalate fiber false twisted yarn of 450 decitex/108f
Ground knitted fabric on the back side: Two twisted yarns of polyethylene terephthalate fiber false twisted yarn of 450 decitex/108f
Connecting fiber: polytrimethylene terephthalate monofilament of 350 decitex/1f (4) Product number: 69030D (by Suminoe Textile Co., Ltd.) Material:
Ground knitted fabric on the front side: Two twisted yarns of polyethylene terephthalate fiber false twisted yarn of 450 decitex/144f
Ground knitted fabric on the back side: Combination of polyethylene terephthalate fiber false twisted yarn of 450 decitex/144f and polytrimethylene terephthalate monofilament of 350 decitex/1f
Connecting fiber: polytrimethylene terephthalate monofilament of 350 decitex/1f (5) Product number: T24053AY5-1S by Asahi Kasei Fibers Corporation The plate-shaped foam bodies 21 and 22 are preferably each formed of a bead foam body. As the bead foam body, for example, a foam molded body molded by a bead method of a resin containing at least one of polystyrene, polypropylene, and polyethylene can be used. The plate-shaped foam bodies 21 and 22 made of a bead foam body propagate a biological signal with micro amplitude as a membrane vibration due to characteristics of a spherical resin film formed by foams constituting individual fine beads. This membrane vibration is transmitted as a string vibration to the three-dimensional knitted material, the membrane vibration and the string vibration are superimposed with each other, and the biological signal is detected by the vibration sensor 30 which will be described later as a mechanical vibration amplified by the superposition of the membrane vibration and the string vibration. Therefore, the detection of the biological signal is facilitated.

If the plate-shaped foam bodies 21 and 22 are each formed of a bead foam body, a foaming factor is preferably within 25 to 50 times and the thickness is formed equal to or less than an average diameter of a bead. For example, if the average diameter of a bead of 30-times foaming is approximately 4 to 6 mm, the plate-shaped foam bodies 21 and 22 are sliced to the thickness of approximately 3 to 5 mm. As a result, flexible elasticity is given to the plate-shaped foam bodies 21 and 22, and solid vibration resonant with a vibration with small amplitude is likely to occur. The plate-shaped foam bodies 21 and 22 may be arranged on the both sides sandwiching the three-dimensional knitted materials 10 as in this embodiment, but may be configured to be arranged only on either one of the sides, preferably only on the seatback side.

Here, as the three-dimensional knitted material 10, a strip-shaped material having a width within a range of 40 to 100 mm and a length within a range of 100 to 300 mm is used. With the material having this size, preliminary compression (state in which a tension is generated in the connecting fiber) is likely to occur in the three-dimensional knitted material 10, and thus an equilibrium state can be easily created between a human being and the three-dimensional knitted material 10. In this embodiment, in order to reduce a sense of discomfort upon abutment of the back part of a human being, two strips are disposed on a target, sandwiching a portion corresponding to the spine. It is preferable that the three-dimensional knitted material 10 is configured to be supported by the three-dimensional knitted material supporting member 15, as shown in FIG. 1, so that the three-dimensional knitted materials 10 can be arranged at predetermined positions easily. The three-dimensional knitted material supporting member 15 is molded in a plate shape, and two vertically long through-holes 15a and 15a for arrangement are formed at symmetrical positions sandwiching the portion corresponding to the spine. The three-dimensional knitted material supporting member 15 is preferably composed of a bead foam body formed in a plate shape, similarly to the above-described plate-shaped foam bodies 21 and 22. The preferable foaming factor and range of thickness if the three-dimensional knitted material supporting member 15 is formed of a bead foam body are the same as those of the above-described plate-shaped foam bodies 21 and 22. However, the thickness of each of the plate-shaped foam bodies 21 and 22 stacked above and below the three-dimensional knitted materials 10 and 10 is preferably smaller than that of the three-dimensional knitted material supporting member 15, in order that the membrane vibration is generated more remarkably by the biological signal.

In a state where the two three-dimensional knitted materials 10 and 10 are inserted into and arranged in the through-holes 15a and 15a for arrangement formed in the three-dimensional knitted material supporting member 15, the films 16 and 16 are laminated on the front side and the back side of the three-dimensional knitted materials 10 and 10. In this embodiment, the peripheral edge portions of the films 16 and 16 are bonded to and laminated on the peripheral portions of the through-holes 15a and 15a for arrangement. The formed positions of the through-holes 15a and 15a for arrangement (that is, the disposed positions of the three-dimensional knitted materials 10 and 10) are preferably set to positions corresponding to regions where a vibration caused by motion involved in pumping of an atrium and aorta (particularly "descending aorta") and motion of an aortic valve can be detected. As a result, the upper and lower surfaces of the three-dimensional knitted materials 10 and 10 are sandwiched by the plate-shaped foam bodies 21 and 22, the peripheral portions are surrounded by the three-dimensional knitted material supporting member 15, and the plate-shaped foam bodies 21 and 22 and the three-dimensional knitted material supporting member 15 function as a resonance box (resonant box). The wall of an aorta is rich in elasticity among arteries and can receive a high pressure of blood directly pumped out of the heart, and an aortic valve which is a valve for preventing a backflow is located immediately out of the left ventricle of the heart. Thus, by arranging the position of the three-dimensional knitted material at the above-described position, the motion of a negative feedback mechanism of the brain and the autonomic nerve system for maintaining homeostasis of a biological body can be well captured.

Moreover, it is preferable that the three-dimensional knitted materials 10 and 10 that are each thicker than the three-dimensional knitted material supporting member 15 be used. That is, such a thickness relationship is established that, when the three-dimensional knitted materials 10 and 10 are arranged in the through holes 15a and 15a for arrangement, the front surfaces and the back surfaces of the three-dimensional knitted materials 10 and 10 protrude from the through holes 15a and 15a for arrangement. As a result, when the peripheral portions of the films 16 and 16 are bonded to the peripheral portions of the through holes 15a and 15a for arrangement, the three-dimensional knitted materials 10 and 10 are pressed in the thickness direction. Therefore, a tensile force caused by a reaction force of the films 16 and 16 is generated, and the solid vibration (membrane vibration) is likely to occur in the films 16 and 16. Meanwhile, preliminary compression occurs also in the three-dimensional knitted materials 10 and 10, and a tension caused by the reaction force is generated also in the connecting fiber maintaining the thickness form of the three-dimensional knitted materials, thereby causing the string vibration readily. The films 16 and 16 are preferably provided on both sides of the front sides and the back sides of the three-dimensional knitted materials 10 and 10, but it is possible to configure such that the film 16 is provided on at least either one of them.

Since the connecting fiber of the three-dimensional knitted materials 10 and 10 extends between the pair of ground knitted fabrics, it becomes a long string wound in a so-called coil shape, and the films 16 and 16 and the plate-shaped foam bodies 21 and 22 functioning as the resonance box (resonant box) are disposed at upper and lower node points. Since the biological signal represented by a heart rate fluctuation has a low frequency, it is amplified by the resonance system provided with the long string and the large number of node points. That is, the string vibration of the connecting fiber causes the membrane vibration of the films 16 and 16 and the membrane vibration of the beads of the plate-shaped foam bodies 21 and 22 to be generated through the large number of node points, whereby they act in a superimposed manner and are amplified. The higher the interval between the node points of the connecting fiber of the three-dimensional knitted materials, that is, the arrangement density of the connecting fiber is, the more preferable it is.

Moreover, it is possible to employ a configuration in which the films 16 and 16 can be arranged on the front side and the back side of the three-dimensional knitted materials 10 and 10 only by bonding the films 16 and 16 on the plate-shaped foam bodies 21 and 22 side in advance to be integrated and by stacking the plate-shaped foam bodies 21 and 22 on the three-dimensional knitted material supporting member 15. However, in order to give the preliminary compression to the three-dimensional knitted materials 10 and 10, the films 16 and 16 are preferably fastened to the surface of the three-dimensional knitted material supporting member 15 as described above. Moreover, instead of disposition of the films in correspondence with each three-dimensional knitted material 10 as in FIG. 1, it is possible to use the film 16 having a size that can cover both the two three-dimensional knitted materials 10 and 10 as shown in FIG. 2.

As the films 16 and 16, a plastic film made of polyurethane elastomer (product number "DUS605-CDR" by Sheedom Co., Ltd., for example) is preferably used in order to capture heart rate fluctuation, for example. However, if natural frequencies of the films 16 and 16 match each other, the membrane vibration is generated by resonance and thus the above is not limiting but those having the natural frequency according to the target to be extracted (heart rate, respiration, atrial and aortic oscillations, and the like) are preferably used. For example, as will be shown in a test example which will be described later, a material with small stretch properties such as an unwoven cloth made of thermoplastic polyester (a biaxial woven fabric (warp: 20 fibers/inch, weft: 20 fibers/inch) formed from a polyethylene naphthalate (PEN) fiber (1100 dtex) by Teijin, for example) can be also used. Moreover, an elastic fiber unwoven cloth having an elongation degree of 200% or more and a recovery rate at 100%-elongation is 80% or more (product name "Espansione" by KB Seiren Ltd., for example) can be also used, for example.

The vibration sensor 30 is fastened to and disposed on either one of the three-dimensional knitted materials 10 before the above-described films 16 and 16 are laminated. The three-dimensional knitted material 10 is composed of a pair of ground knitted fabrics and the connecting fiber, and since the string vibration of each connecting fiber is transmitted to the films 16 and 16 and the plate-shaped foam bodies 21 and 22 through the node points with the ground knitted fabrics, a sensing portion 30a of the vibration sensor 30 is preferably fastened to the surface of the three-dimensional knitted material 10 (surface of the ground knitted fabric). As the vibration sensor 30, a microphone sensor or particularly a capacitor-type microphone sensor is preferably used. In this embodiment, since it is not necessary to consider sealing performance at a portion where the microphone sensor is disposed (that is, the through hole 15a for arrangement in which the three-dimensional knitted material 10 is disposed), a lead wire of the microphone sensor can be wired easily. In this embodiment, as described above, the vibration on the body surface through the muscle of a human being involved in the biological signal is propagated not only to the three-dimensional knitted material 10 but also to the plate-shaped foam bodies 21 and 22 and the film 16, and they are vibrated (string vibration, membrane vibration), and are superposed and amplified. Thus, the vibration sensor 30 can fix the sensing portion 30a not only to the three-dimensional knitted material 10 but also to the plate-shaped foam bodies 21 and 22 and the film 16 constituting a vibration transmission path. In this embodiment, since the three-dimensional knitted material 10, the three-dimensional knitted material supporting member 15, the plate-shaped foam bodies 21 and 22, and the film 16 constitute the mechanical amplification device, in order to mechanically amplify the biological signal.

The biological signal measuring means 1, as described above, is arranged inside a skin 120 covering a seatback frame 110 of the vehicle seat 100 as shown in FIG. 3, for example. In order to facilitate an arrangement work, the three-dimensional knitted material 10, the three-dimensional knitted material supporting member 15, the film 16, the plate-shaped foam bodies 21 and 22, the vibration sensor 30 and the like that constitute the biological signal measuring means 1 are preferably unitized in advance.

The above-described biological signal measuring means 1 has a mechanical amplification device provided with the three-dimensional knitted material 10 and the plate-shaped foam bodies 21 and 22 stacked around the three-dimensional knitted material 10, preferably a mechanical amplification device in which a film 16 is disposed between the three-dimensional knitted material 10 and the plate-shaped foam bodies 21 and 22. The biological signal measuring means 1 is configured such that a vibration sensor is attached to this mechanical amplification device. A micro vibration of the body surface caused by a biological signal of a human being, such as heart rate, respiration, atrial and aortic vibrations, and the like, is propagated to the plate-shaped foam bodies 21 and 22, the film 16, and the three-dimensional knitted material 10, and a membrane vibration is generated in the plate-shaped foam bodies 21 and 22 and the film 16, while a string vibration of a fiber is generated in the three-dimensional knitted material.

Moreover, the three-dimensional knitted material 10 is formed such that the connecting fibers are disposed between the pair of ground knitted fabrics and is provided with a load-deflection characteristic close to the load-deflection characteristic of a human muscle. Therefore, by making the load-deflection characteristic of the mechanical amplification device including the three-dimensional knitted material 10 be close to that of a muscle and by disposing the device adjacent to the muscle, respective differences in internal and external pressures between the muscle and the three-dimensional knitted material becomes equal, and a biological signal, such as heart rate, respiration, atrial and aortic vibrations, and the like, can be transmitted accurately, whereby the string vibration can be generated in a fiber (or particularly the connecting fiber) constituting the three-dimensional knitted material 10. Moreover, the plate-shaped foam bodies 21 and 22 stacked on the three-dimensional knitted material 10, preferably a bead foam body, is likely to generate a membrane vibration in each bead due to the flexible elasticity and small density of the bead. The film 16 is likely to generate membrane vibration readily, since a predetermined tension is generated by means of fixing the peripheral portion of the film 16 and elastically supporting the film 16 by the three-dimensional knitted material close to the load-deflection characteristic of a human muscle. That is, according to the biological signal measuring means 1, the membrane vibration is generated in the plate-shaped foam bodies 21 and 22 and the film 16 in the mechanical amplification device having the load-deflection characteristic close to the load-deflection characteristic of the muscle by a biological signal, such as heart rate, respiration, atrial and aortic vibrations, and the like, and the string vibration is generated in the three-dimensional knitted material 10 having the load-deflection characteristic close to the load-deflection characteristic of the human muscle. The string vibration of the three-dimensional knitted material 10 influences the membrane vibration of the film 16 and the like again, and these vibrations act in a superimposed manner. As a result, the vibration inputted from the body surface with the biological signal is directly detected by the vibration sensor 30 as solid vibration amplified by superposition of the string vibration and the membrane vibration.

As the biological signal measuring means 1 used in the present invention, a configuration which detects an air pressure fluctuation within a sealed bag as before can be used, but since a volume and pressure are inversely proportional to each other, it is difficult to detect a pressure fluctuation unless the volume of the sealing bag is made small. Meanwhile, since the biological signal measuring means 1, as described above, detects an amplified solid vibration transmitted to the mechanical amplification device (the three-dimensional knitted material 10, the plate-shaped foam bodies 21 and 22, and the film 16), as described above, instead of the air pressure fluctuation, the volume (cubic volume) is hardly limited from the viewpoint of detection sensitivity, so that a vibration with small amplitude involved in heart rate, respiration, atrial and aortic oscillations, and the like can be detected with a high sensitivity. Therefore, the means can accommodate persons having various physical builds. Accordingly, the biological signal measuring means 1 can detect a biological signal with a high sensitivity even under an environment, such as a vehicle seat, used by people with various physical sizes and into which various external vibrations are inputted. Moreover, since it is not necessary to form a sealed structure, a manufacturing process is simplified, and a manufacturing cost is lowered, which are suitable for mass production.

The above-described biological signal measuring means 1 is incorporated in the inside of a skin 120 of the seat 100 but may be incorporated in a seat cushion attached to the surface of the skin 120 afterwards. However, in the case of attachment afterwards, it is preferable to provide a hard face such as a three-dimensional knitted material with high planar stiffness or to insert a plate having a thickness of approximately 1 to 2 mm made of a synthetic resin such as polypropylene between the seat and the three-dimensional knitted material so that preliminary compression can be easily generated in the three-dimensional knitted material by the body weight. For example, in the case of a seat with soft compression characteristics, the three-dimensional knitted material is not preliminarily compressed and thus, a biological signal is not reflected but absorbed. However, by providing a hard face as above, the fluctuation in the compression characteristics on the seat side as above is absorbed, and a biological signal with large amplitude can be obtained readily.

Figure 4:
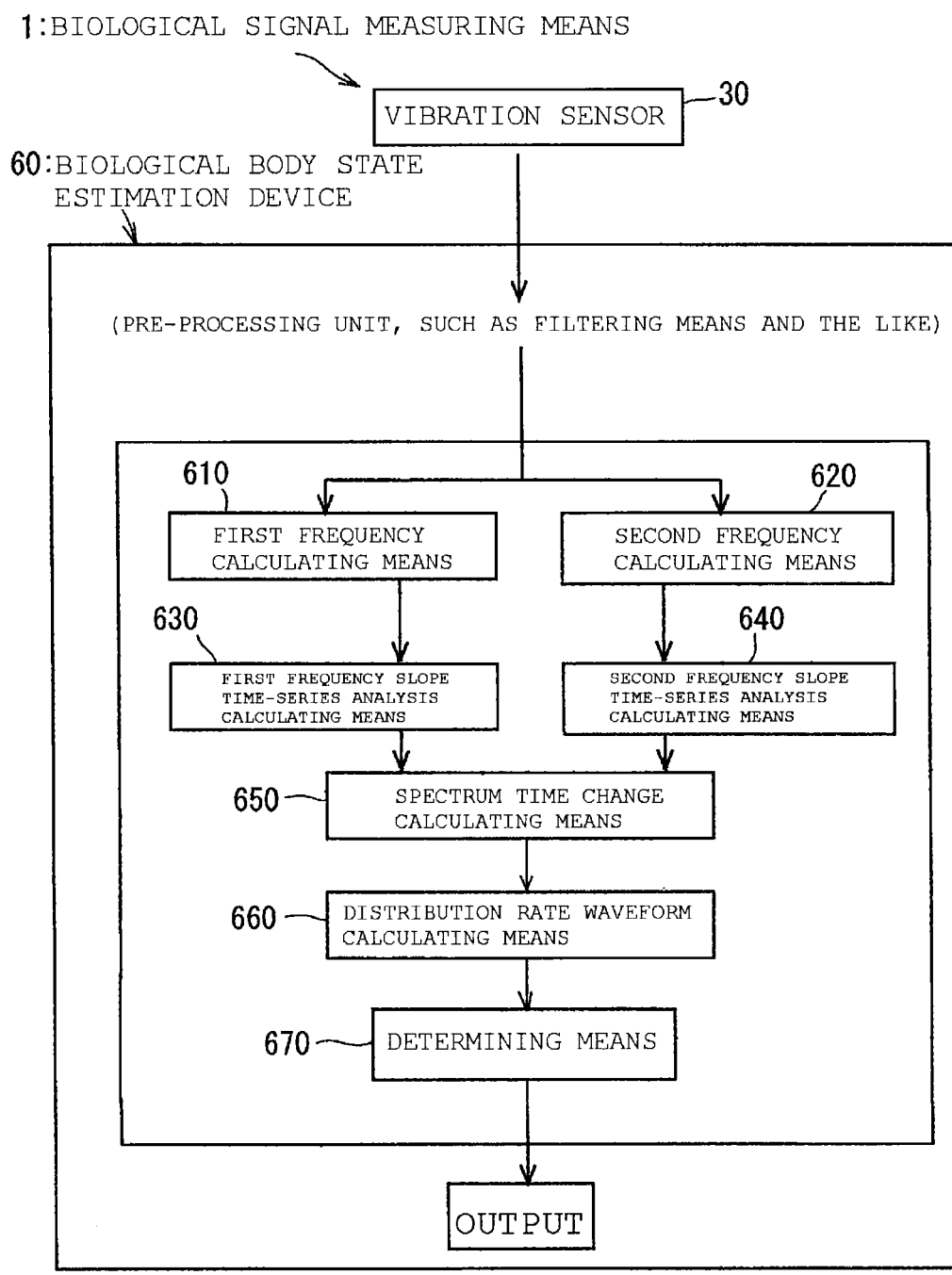
FIG. 4 is a diagram showing a configuration of a biological body state estimation device according to an embodiment of the present invention.

Next, a description will be given of a configuration of the biological body state estimation device 60, on the basis of FIG. 4. The biological body state estimation device 60 includes first frequency calculating means 610 and second frequency calculating means 620 as frequency calculating means, and includes first frequency slope time-series analysis calculating means 630 and second frequency slope time-series analysis calculating means 640 as frequency slope time-series calculating means. Furthermore, the biological body state estimation device 60 includes a spectrum time-series change calculating means 650, a distribution rate waveform calculating means 660, and a determining means 670. The biological body state estimation device 60 is constituted by a computer, and a computer program is set, which causes the computer to perform: first and second frequency calculation steps that constitute a frequency calculation step; first and second frequency slope time-series analysis calculation steps that constitute a frequency slope time-series calculation step; a spectrum time-series change calculation step; a distribution rate waveform calculation step; and a determining step. Note that the computer program may be provided while being stored in a recording medium, including a flexible disk, a hard disk, a CD-ROM, an MO (magneto-optical disk), a DVD-ROM, and a memory card, or may also be transmitted via a communication line.

Each of the first and second frequency calculating means 610 and 620 determines a time-series waveform of a frequency for time-series data of an output signal obtained from the vibration sensor 30 of the biological signal measuring means 1, or preferably for time-series data in a predetermined frequency region subjected to a filtering process (for example, a filtering process of removing low frequency components of 0.01 Hz or lower which is caused due to the body motion and the like). Of them, the first frequency calculating means 610 is related to LF/HF for use as an index of a sympathetic nervous function, and the second frequency calculating means 620 is related to HF for use as an index of a parasympathetic nervous function.

Figure 5:
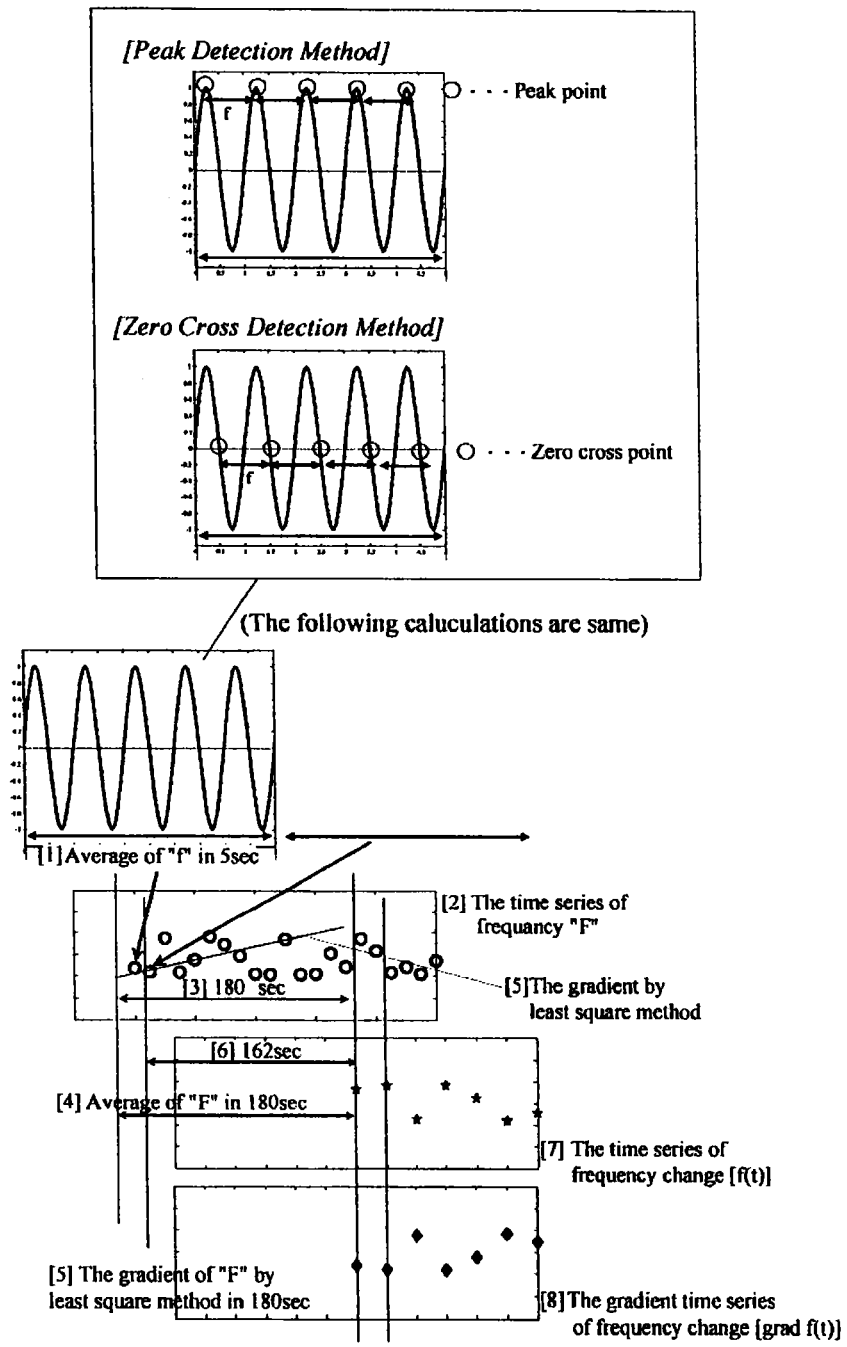
FIG. 5 is a diagram for explaining a method of determining a frequency slope time-series waveform by using a peak value or a zero-crossing point of a biological signal detected by the biological signal measuring means.

In more detail, the first frequency calculating means 610 is a method (hereinafter, referred to as a "zero crossing method") of determining a time-series waveform of a frequency for a time-series waveform of an output signal obtained from the vibration sensor of the biological signal measuring means 1 by using points (hereinafter, referred to as "zero-crossing points") at each of which a positive of the time-series waveform is switched to a negative. This zero-crossing method is to capture a fundamental component of a frequency of a biological signal, and indicates whether a frequency balanced state is present or absent due to an effect of an adjustment function in a nerve center, which is a negative feedback mechanism in a frequency adjustment, thereby indicating an intensity level of emergence of LF/HF. In this method, zero-crossing points are first determined; they are divided into parts of 5 seconds; a reciprocal number of a time interval between zero-crossing points of a time-series waveform which are contained in the part of 5 seconds is determined as an individual frequency f; and an average of the individual frequencies f in 5 seconds is employed as a value of a frequency F for 5 seconds (step [1] in FIG. 5). Then, a time-series waveform of the frequency is determined by plotting the frequencies F obtained every 5 seconds (step [2] in FIG. 5).

The second frequency calculating means 620 is a method (hereinafter, referred to as a "peak detection method") of determining a time-series waveform by smoothing and differentiating a time-series waveform of the output signal obtained from the vibration sensor of the biological signal measuring means 1 and by using maximum values (peak values). The peak detection method is basically a time-series waveform corresponding to a function of HF. For example, the maximum values are determined by the smoothing differentiation method of Savitzky and Golay. Next, the maximum values are divided into parts of 5 seconds; a reciprocal number of a time interval between maximum values (peak portions of the crest of the waveform) of a time-series waveform which are contained in the part of 5 seconds is determined as an individual frequency f; and an average of the individual frequencies f in 5 seconds is employed as a value of a frequency F for 5 seconds (step [1] in FIG. 5). Then, a time-series waveform of the frequency is determined by plotting the frequencies F obtained every 5 seconds (step [2] in FIG. 5).

Each of the first and second frequency slope time-series analysis calculating means 630 and 640 is configured: to set time windows of a predetermined time width from the time-series waveform of the frequency of the output signal from the vibration sensor of the biological signal measuring means 1, which the first frequency calculating means 610/the second frequency calculating means 620 obtains by using the zero-crossing method or the peak detection method; to determine a slope of the frequency of the output signal from the vibration sensor for each time window by using the least-square method; and to output a time-series waveform of the slope. In more detail, slopes of a frequency in any given certain time window Tw1 are obtained by the least-square method, and are plotted (steps [3] and [5] in FIG. 5). Then, a subsequent time window Tw2 is set in an overlap time T1 (step [6] in FIG. 5), and slopes of the frequency in this time window Tw2 are acquired with the least-square method and are plotted in a similar manner. This calculation (movement calculation) is sequentially repeated, and a time-series change in a slope of a frequency of an air pack signal is outputted as a frequency slope time-series waveform (step [8] in FIG. 5). Note that the time width of each time window Tw is preferably set to 180 seconds, and the overlap time T1 is preferably set to 162 seconds. The reason is that they are selected as values at which a characteristic signal waveform emerges with the highest sensitivity through sleep experiments conducted by changing the time widths of the time window Tw and the overlap time T1, as shown in the above-described Patent Literature 3 (WO2005/092193A1) filed by the applicant of this application.

As described above, it is said that a characteristic of a fluctuation of atrial fibrillation is switched at 0.0033 Hz, and fluctuations for adjusting the fluctuation of 0.0033 Hz are present in the vicinity of and lower than 0.0033 Hz. Accordingly, looking at a state of a fluctuation centered at 0.0017 Hz that is in a middle point between 0 Hz and 0.0033 Hz, a rough outline of a state of the fluctuation generated at 0.0033 Hz or lower is considered to appear even if the fluctuation varies. A time that corresponds to ¼ of a period of a waveform of 0.0017 Hz is 147 seconds. Assuming that the waveform is smoothed under the condition that a lap is 90%, if before and after times of 10% is added, "147/0.8=approximately 180 seconds" is satisfied. Even in this regard, 180 seconds are said to be preferable. Here, a manner of a change, a tendency of the change, a differential coefficient, and a slope over 3 minutes are captured every 180 seconds, as time-series waveforms. Then, a time of 180 seconds is lapped by 90% in order to smooth a slope that is an average in 180 seconds; a time-series waveform is created by plotting the slopes for 18 seconds; and the time-series waveform of this slope is used to conduct an analysis. This slope time-series waveform is used to capture a constant fluctuation, and to broadly evaluate a degree of controlling a heart rate variation, as a time-series waveform.

The first frequency slope time-series analysis calculating means 630 is means for determining a frequency slope time-series waveform from the time-series waveform of the frequency which the first frequency calculating means 610 obtains by using the zero-crossing method. The second frequency slope time-series analysis calculating means 640 is means for determining a frequency slope time-series waveform from the time-series waveform of the frequency which the second frequency calculating means 620 obtains by using the peak detection method. The frequency slope time-series waveform which the first frequency slope time-series analysis calculating means 630 obtains by using the zero-crossing method (0x detection method) indicates a fluctuation of a biological body which captures a balance of emergencies of the sympathetic nerve and the parasympathetic nerve. The time-series waveform which the second frequency slope time-series analysis calculating means 640 obtains by using the peak detection method indicates a fluctuation of a biological body which captures a state of the parasympathetic nerve.

The spectrum time-series change calculating means 650 is means for analyzing respective frequencies of the frequency slope time-series waveform obtained from the first frequency slope time-series analysis calculating means 630 and the frequency slope time-series waveform obtained from the second frequency slope time-series analysis calculating means 640, and for determining respective power spectrums of frequencies corresponding to the above functional adjustment signal, fatigue reception signal, and activity adjustment signal.

The distribution rate waveform calculating means 660 extracts preset frequency components corresponding to the functional adjustment signal, fatigue reception signal and activity adjustment signal from a time-series change in the power spectrums obtained by the spectrum time-series change calculating means 650; calculates respective proportions of the three frequency components in time sequence under the condition that a sum of values of the power spectrums of the three frequency components is 100; and determines respective time-series variation waveforms of the power spectrums as distribution rate waveforms. Here, in this embodiment, 0.0017 Hz, 0.0035 Hz and 0.0053 Hz are a functional adjustment signal, a fatigue reception signal, and an activity adjustment signal, respectively, as described above. The validity of these frequencies will be described in detail with a test example that will be described later.

The determining means 670 locates a wave change pattern of the above three frequency components in the distribution rate waveforms obtained by the distribution rate waveform calculating means 660, and determines a state of a human being by comparing the located waveform change pattern with correlation data regarding waveform change patterns and states of a human being which is stored in a storage unit in advance.

As waveform change patterns, a pattern in which the functional adjustment signal (0.0017 Hz) and the fatigue reception signal (0.0035 Hz) appear with both phases opposite to each other, and a pattern in which the functional adjustment signal (0.0017 Hz) and the fatigue reception signal (0.0035 Hz) appear with both phases opposite to each other and the activity adjustment signal (0.0053 Hz) has a distribution rate of a predetermined value or higher are cited. These waveform change patterns are stored in the storage unit (a hard disk or the like) of the biological body state determination device 1 in advance. The storage unit also stores correlation data regarding the waveform change patterns and states of a human being. The determining means 670 compares the waveform change pattern of the three signals in a predetermined time zone which are being measured and each of the stored waveform change patterns, and identifies one of the patterns to which the waveform change pattern corresponds. Then, the determining means 670 determines a state of a human being which corresponds to the located waveform change pattern, from the above correlation data.

TEST EXAMPLE (Test Contents)

The biological signal measuring means 1 shown in FIG. 1 was stacked on the back side of the back portion of a seat cushion which had a product name of "Twin lumbar" and was produced by Delta Tooling Co. Ltd., and was attached to an automobile seat installed indoors; each human subject was made to sit; biological signals generated by the atrial and aortic oscillations (hereinafter referred to as a "heart-part oscillation wave", but may also be described as "AMP" for short) were acquired; and a sleep introduction experiment was conducted. For the plate-shaped foam bodies 21 and 22 and the three-dimensional knitted material supporting member 15 that constituted the biological signal measuring means 1, a bead foam body was used in which an average diameter of a bead was approximately 5 mm and which was sliced to have a thickness of 3 mm. The three-dimensional knitted material 10 was produced by Suminoe Textile Co., Ltd., and had a product number of 49011D and a thickness of 10 mm. For the film 16, one which was produced by Sheedom Co., Ltd. and had a product number of "DUS605-CDR" was used.

In the sleep introduction experiment, each human subject was obliged to resist sleepiness and to keep an awake state for 30 minutes from the start of the experiment, within an isolated indoor space with few people. After 30 minutes passed, each human subject was allowed to behave in accordance with his/her intent, and those who wanted to sleep were permitted to sleep, whereas those who wanted to keep awake were permitted to keep awake. However, if they fell asleep, they were awakened immediately.

In the sleep introduction experiment, conventional medical indices, such as brain waves, electrocardiograms, and fingertip plethysmograms, were also acquired in addition to the heart-part oscillation waves. The brain waves were measured by using an electroencephalograph ("EEG-9100, Neurofax μ" by Nihon Kohden Corporation), and the fingertip plethysmograms were measured by attaching a fingertip plethysmogram meter (finger clip probe SR-5C by AMCO Inc.).

Figure 6A:
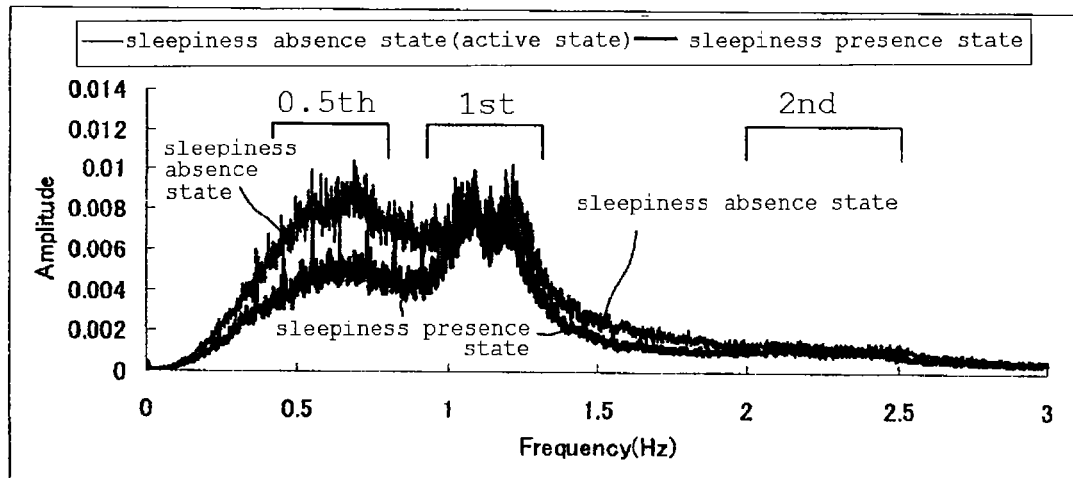
FIG. 6A shows a frequency analysis result of data created by merging original waveforms of heart-part oscillation waves of 22 human subjects in sleepiness absence state (active state) in a sleep introduction experiment, and a frequency analysis result of data created by merging the original waveforms of the heart-part oscillation waves in a sleepiness present state.

FIG. 6A shows a frequency analysis result of data produced by merging together original waveforms of heart-part oscillation waves of 22 human subjects in the state where they have no sleepiness (during an awake period), and a frequency analysis result of data produced by merging together original waveforms of heart-part oscillation waves in the state where they have sleepiness (during a period of resisting sleeping), in the sleep introduction experiment.

Since peaks are present at 0.6 Hz and 1.2 Hz during the awake period, 0.6 Hz and 1.2 Hz are components of the heart motion and the pulse wave, and they are considered to control the number of heart rates. However, when the fatigue is increased and the sleepiness arises, the heart motion becomes stable due to the compensation effect of the sympathetic nervous, and the motions of the pulse wave and the heart at 1.2 Hz are dominated. The energy for the motion of the heart is minimized by performing the control at a higher frequency. Thus, the homeostasis is considered to be maintained by reducing the energy consumption, in order to maintain the function of the body for a long time upon fatigue. The APW in which components of the heart motion and the pulse wave appear is mainly composed of a band centered at a frequency component of ⅓ to ½ of the heart rate (0.5th), a band of the heart rate (1st), and a component of twice of the heart rate (2nd). This shows the reduction in a chaos performance. In the low dimensional chaos, the energy consumption is reduced, and therefore the mechanical energy consumption is suppressed at the minimum.

Figure 6B:
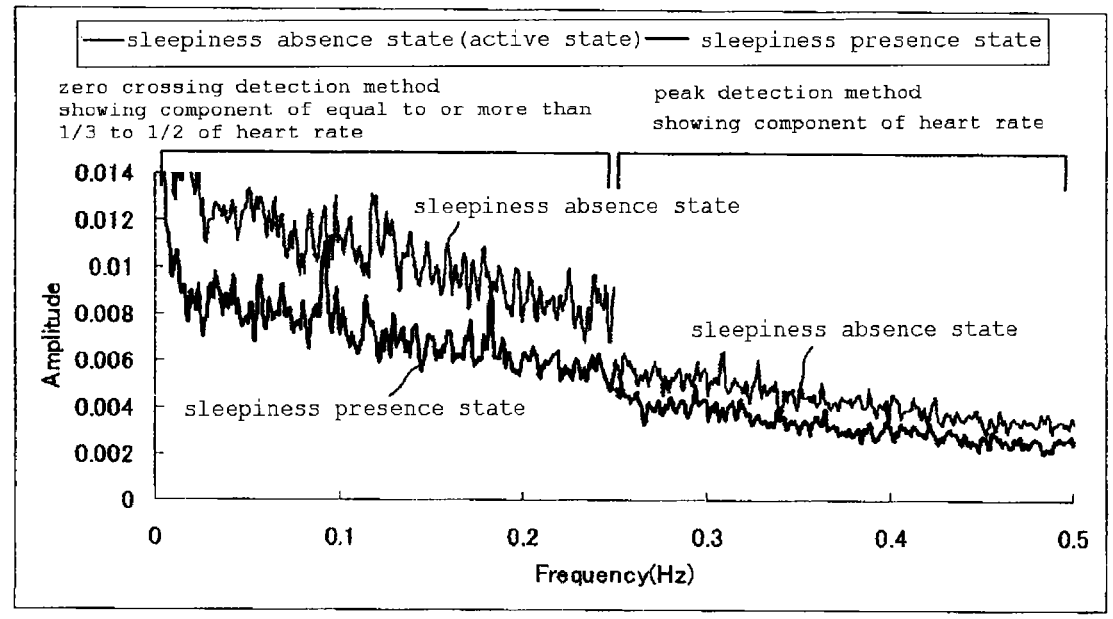
FIG. 6B is a diagram showing a frequency analysis result of time-series waveforms produced by subjecting the zero crossing detection method and the peak detection method to the APWs individually acquired for the presence and absence of the sleepiness shown in FIG. 6A.

FIG. 6B shows a frequency analysis result of time-series waveforms produced by subjecting the zero crossing detection method and the peak detection method to the APWs individually acquired for the presence and absence of the sleepiness shown in FIG. 6A. A component related to the heart rate which is generated by the peak detection method is disposed at 0.25 Hz (¼ Hz) or higher, and a component mainly having components of ⅓ to ½ of the heart rate (⅛ to 1/12 Hz) is shown. A component produced by the zero crossing detection method is disposed at 0.25 Hz or lower. It can be seen that this tendency is closely related to that of FIG. 6A.

Figure 7A:
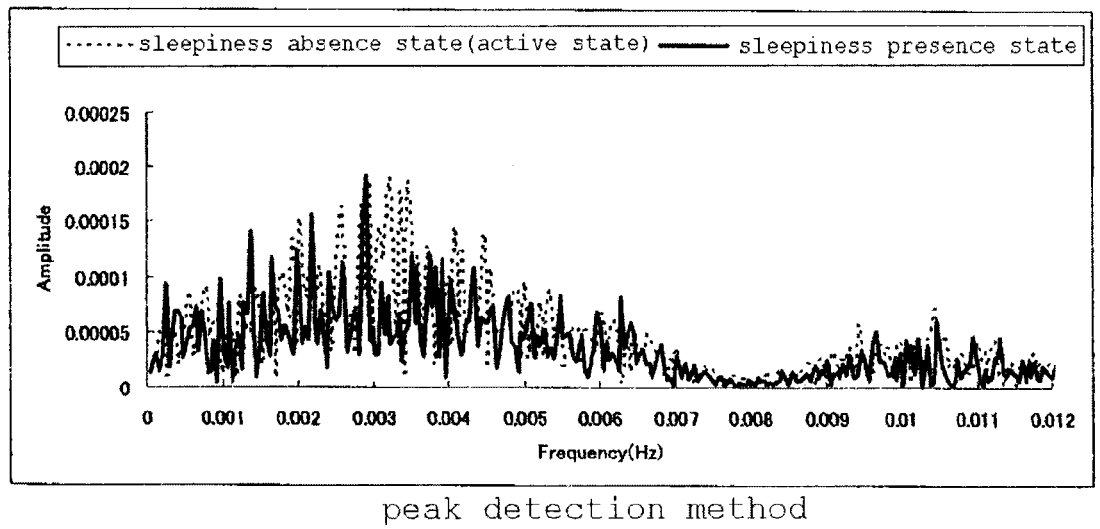
FIGS. 7A and B are diagrams showing frequency analysis results of the slope time-series waveform that is produced from the APWs of FIG. 6A: A is the result obtained by using the peak detection method; and B is the result obtained by using the zero-crossing method.
Figure 7B:
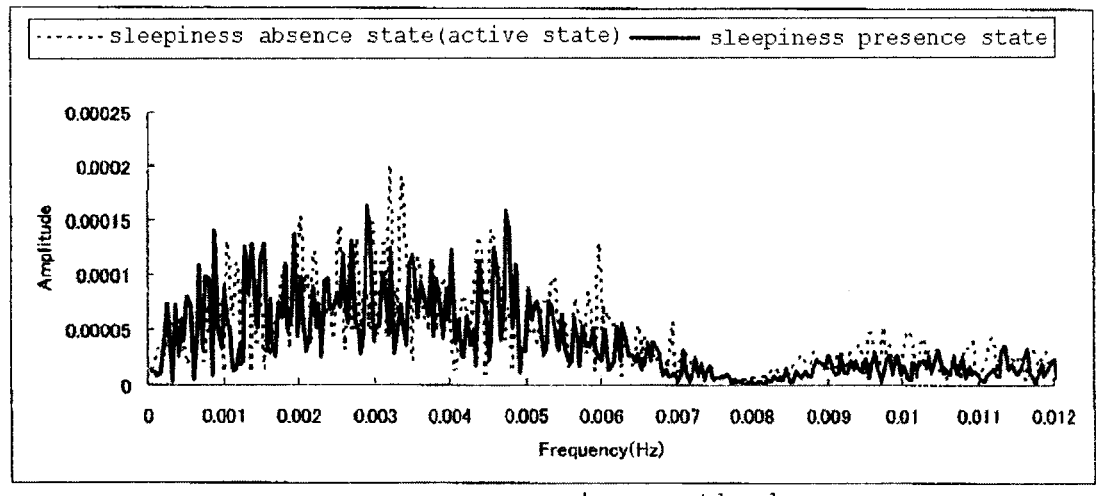

FIGS. 7A and B show a frequency analysis result of a slope time-series waveforms produced from the APWs of FIG. 6A: the peak detection method is used in A; and the zero-crossing method is used in B. Comparing FIG. 6A with 6B, the difference is small between the sleepiness presence state and the sleepiness absence state, but the tendency of the relation to FIGS. 6A and B is maintained.

Figure 8:
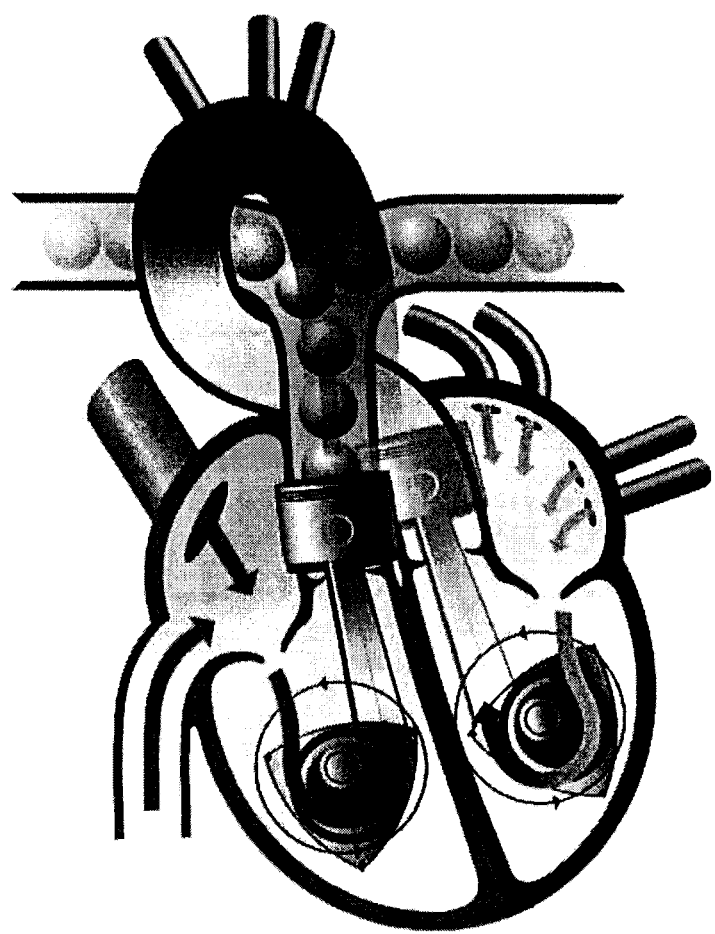
FIG. 8 is a diagram of a heart model when a heart is likened to a piston and crank mechanism.

As for the motions of the heart and the pulse wave (heart-part oscillation wave (APW)) generated in the aortic, a heart model is assumed as shown in FIG. 8, and in the case where a force generated in the aortic is determined by likening the heart model to a piston and crank mechanism, the force is as shown in FIG. 9. In this case, the force is determined from a sum of a factor continuously changing over a period of the expansion and contraction of the heart and a factor having a period of a half of the above period, and matches the primary and secondary inertial force components of FIG. 6A.

Figure 10:
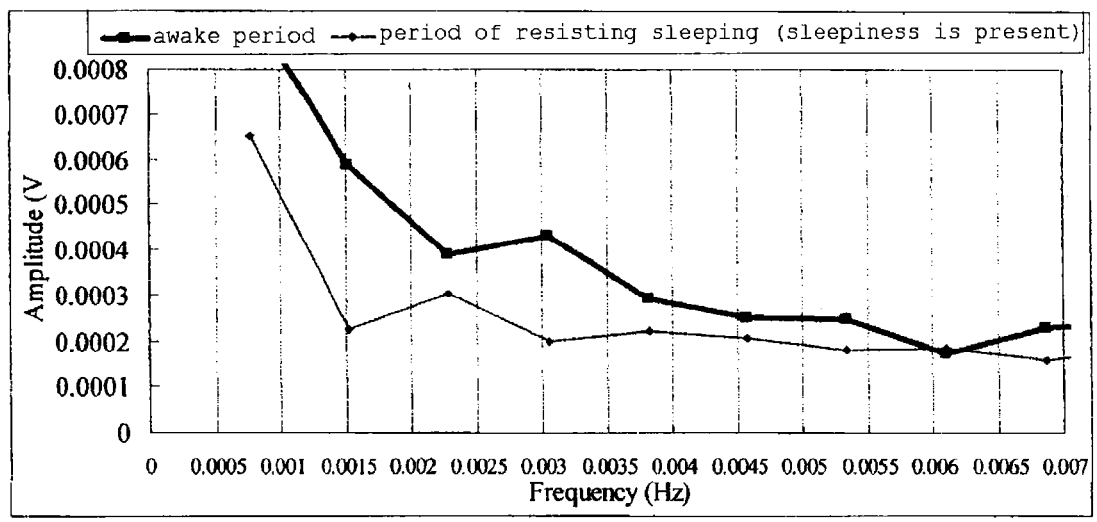
FIG. 10 is a diagram showing a super low frequency band (0 to 0.007 Hz) of a frequency spectrum produced by analyzing a frequency of the merged data of the heart-part oscillation waves shown in FIG. 6A.

FIG. 10 shows a super low frequency band (0 to 0.007 Hz) of frequency spectrums generated by analyzing the frequencies of the merged data of the heart-part oscillation waves as shown in FIG. 6A. In comparison with the awake period, low frequency components are lower during a period of resisting sleeping (in a sleepiness presence state), and it can be seen that even the super low frequency region reflects the whole change. It can be seen from FIG. 10 that the frequency spectrums change at 0.0015 Hz, 0.0023 Hz and 0.003 Hz. In view of this, it is said that points at which the cardiovascular dynamic behavior is switched are present at 0.0035 Hz or lower. This is highly possible, in the light of the fact that the point at which the atrial fibrillation is switched is 0.0033 Hz as described above.

Figure 11:
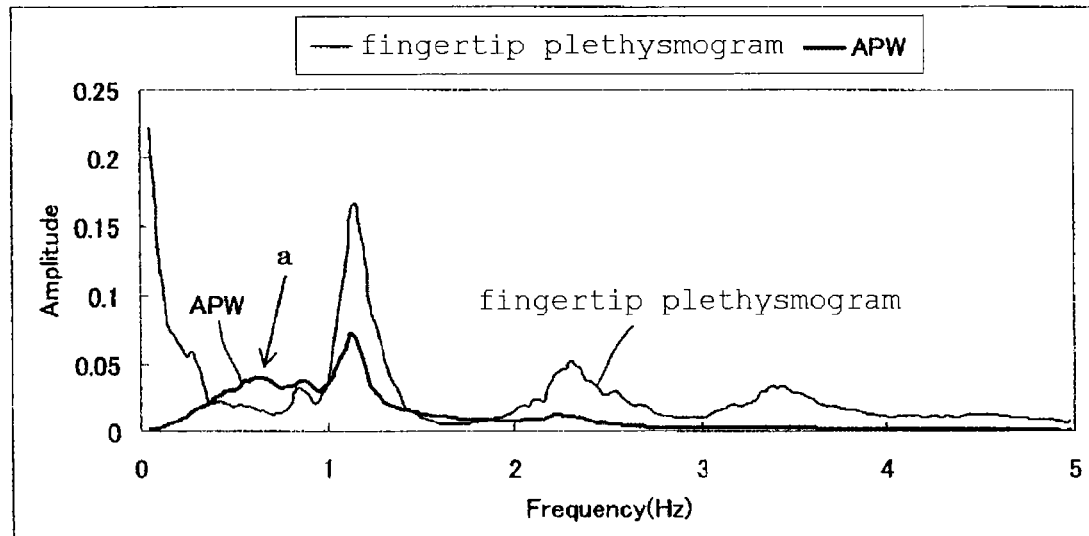
FIG. 11 is a diagram showing a frequency analysis result of a fingertip plethysmogram and an APW.

FIG. 11 shows a frequency analysis result of the fingertip plethysmogram and the APW. It can be seen that the fingertip plethysmogram is characterized by a high frequency component due to the secondary inertial force, and the APW is characterized by a band indicated in a low frequency component (arrow a).

Figure 12:
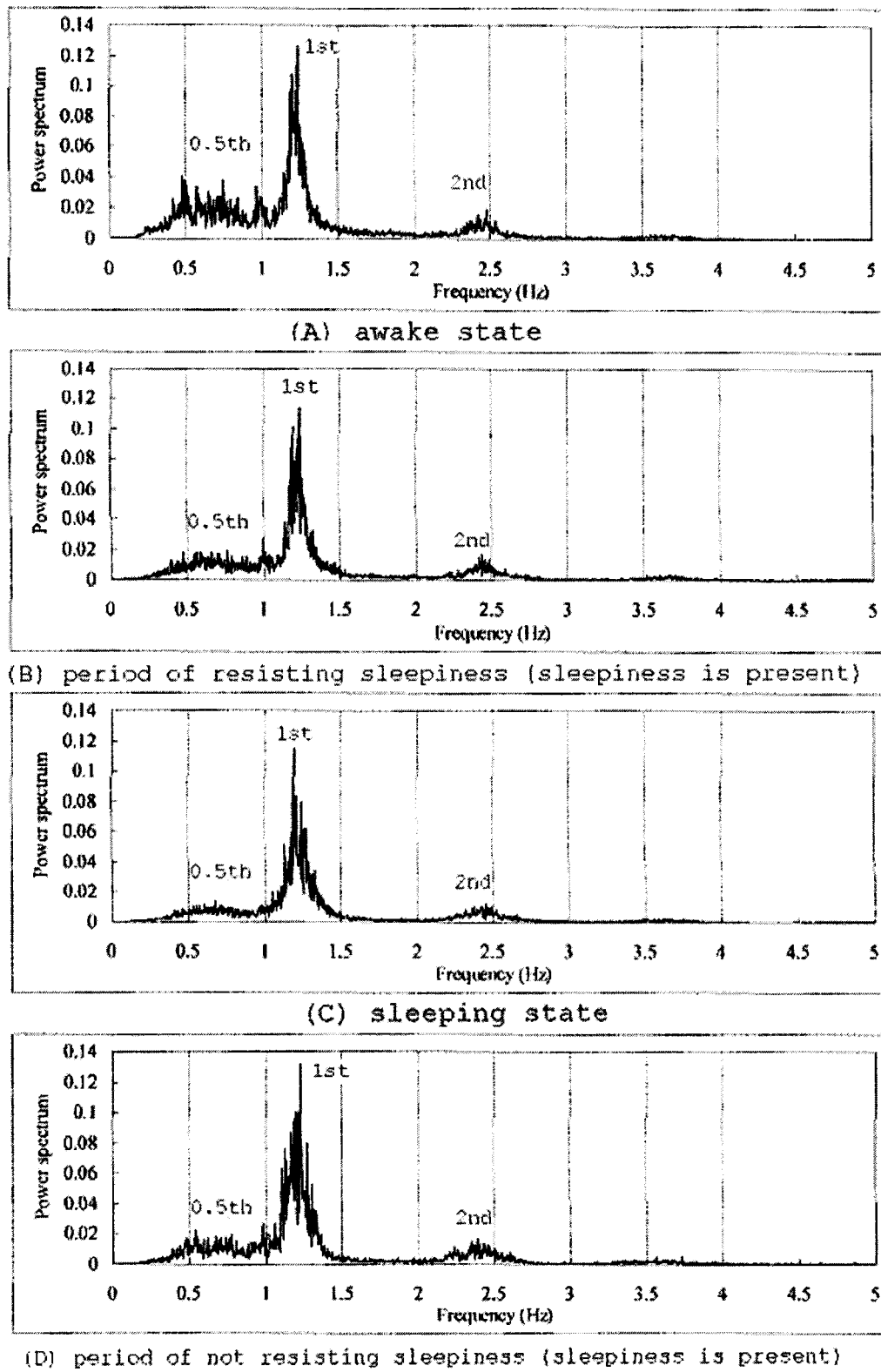
FIGS. 12A to D are diagrams showing frequency analysis results of heart-part oscillation waves for individual states, in the sleep introduction experiment.

FIG. 12 shows a frequency analysis result of the heart-part oscillation waves for individual states, in the sleep introduction experiment. As an awake state is being changed into a sleeping state, a power spectrum in a frequency range of ½ of the heart rate component is decreasing, and a peak of the spectrum of the heart rate component is being shifted toward the lower frequency. Then, a sleepiness presence state after awakening returns to the former state. This suggests that the cardiovascular dynamic behavior is changed at the same time of the change in the states. Even in this case, 0.5th, 1st and 2nd components appear prominently.

FIGS. 13 and 14 show a frequency analysis result of a slope time-series waveform of a frequency of the heart-part oscillation wave, in the sleep introduction experiment. FIG. 13 is an analysis result of a slope time-series waveform of a frequency which the first frequency slope time-series analysis calculating means 630 obtains by employing the zero-crossing method (0x detection method), and FIG. 14 is an analysis result of a slope time-series waveform of a frequency which the second frequency slope time-series analysis calculating means 640 obtains by employing the peak detection method.

FIGS. 13A and 14A show a spectrum of each human subject of the 22 human subjects in the sleep introduction experiment, and FIGS. 13B and 14B show results of totalizing the spectrums of FIGS. 13A and 14A in steps of 0.0001 Hz. FIGS. 13C and 14C are frequency analysis results of the data, after slope time-series waveforms of frequencies for 36 human subjects in the sleep introduction experiment are merged into a single piece of data. It can be seen that the frequency analysis results of the slope time-series waveforms of the frequencies exhibit a higher fractionation sensibility in comparison with the frequency analysis result of the original waveform of the heart-part oscillation wave in FIG. 6.

In FIGS. 13A and B and FIGS. 14 A and B, when a center of the variation is determined by a band of the lowest frequency, the center becomes 0.0017 Hz, and border lines are drawn on the assumption that the center is present at 0.0033 Hz in the subsequent band and at 0.0053 Hz in the subsequent band. In this case, a similar tendency can be observed even in FIGS. 13C and 14C. In more detail, it can be seen that a variation is recognized in super low frequency bands centered in three frequency bands of 0.0017 Hz, 0.0035 Hz and 0.0053 Hz. In this case, the fluctuation that varies in a band of 0.0017 Hz to 0.0053 Hz is changed depending on a health condition and the degree of progress of fatigue, and this changing manner is considered to enable a state of a human being to be captured. This suggests a possibility in which the homeostasis maintenance function of the heart is present with a variation within a frequency band of a very low frequency which is centered at 3 minutes.

Here, inversely, it is considered whether or not it is possible to determine an APW from the three frequencies (0.0017 Hz, 0.0033 Hz and 0.0053 Hz). FIG. 15A shows a comparison among an APW, a waveform obtained by subjecting the APW to the zero crossing detection process, and a slope time-series waveform produced by the zero crossing detection method. FIG. 15B shows a comparison between a synthetic waveform of sinusoidal waves of 0.0017 Hz, 0.0035 Hz and 0.0053 Hz and the slope time-series waveform produced by the zero crossing detection method. FIG. 15C shows a comparison of a frequency analysis result between the synthetic waveform and the slope time-series waveform produced by the zero crossing detection method. FIG. 16A shows a comparison between among an APW, a waveform obtained by subjecting the APW to the peak detection process, and a slope time-series waveform produced by the peak detection method. FIG. 16B shows a comparison between a synthetic waveform of sinusoidal waves of 0.0017 Hz, 0.0035 Hz and 0.0053 Hz and the slope time-series waveform produced by the peak detection method. FIG. 16C shows a comparison of a frequency analysis result between the synthetic waveform and the slope time-series waveform produced by the peak detection method. Since the synthetic waveform of the sinusoidal waves of 0.0017 Hz, 0.0035 Hz and 0.0053 Hz is approximate to the slope time-series waveform of the APW, 0.0017 Hz, 0.0033 Hz and 0.0053 Hz are considered to indicate the degree of control for homeostasis maintenance prominently.

Figure 17:
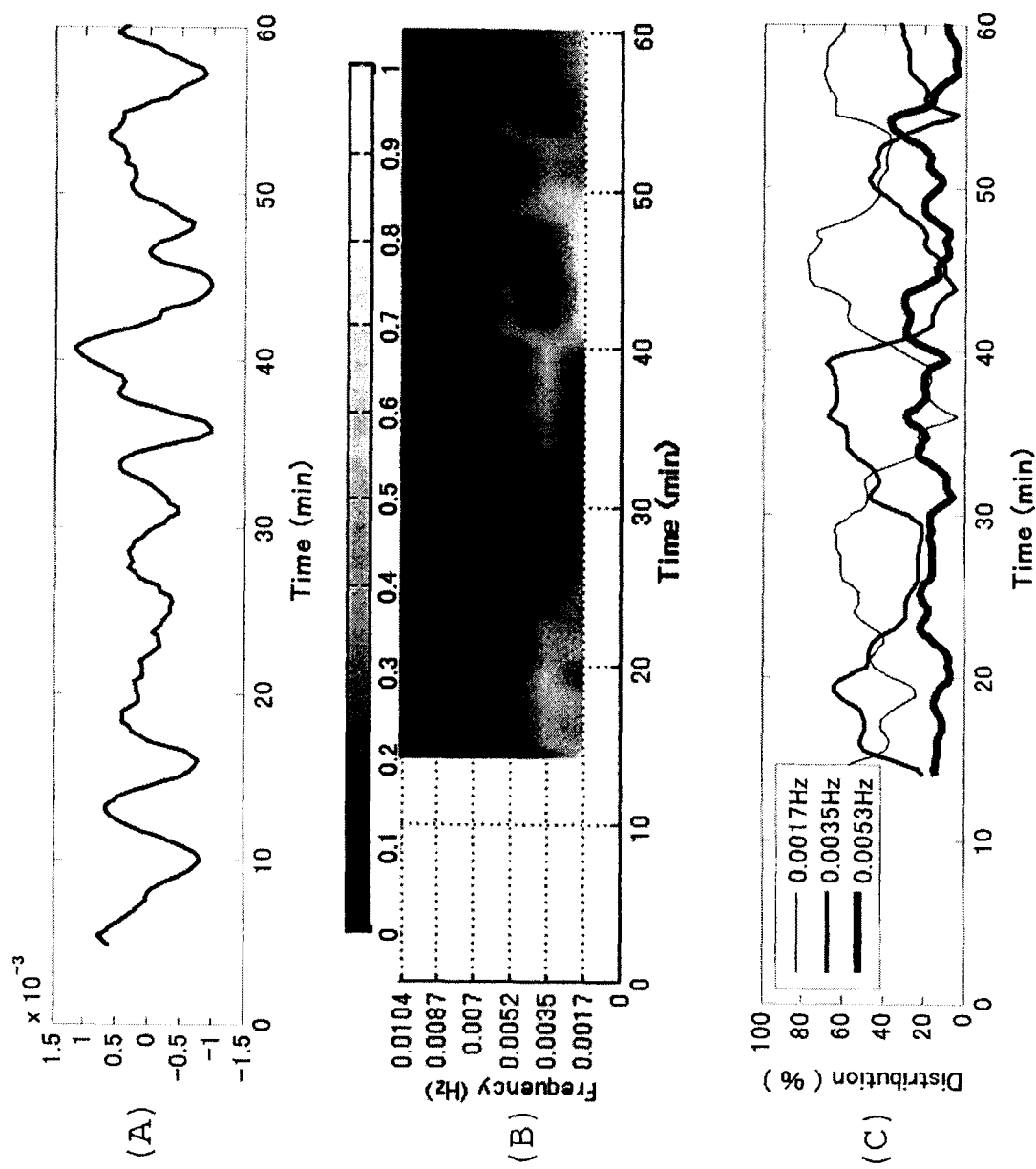
FIGS. 17A to C are diagrams for explaining how to determine distribution rates of three frequency components of 0.0017 Hz, 0.0033 Hz, and 0.0053 Hz.

Next, a description will be given of a specific method of determining distribution rates of the three frequency components. As shown in FIG. 17A, first, the first frequency slope time-series analysis calculating means 630 or the second frequency slope time-series analysis calculating means 640 determines a frequency slope time-series waveform by using the zero-crossing method (0x detection method) or the peak detection method. As shown in FIG. 17B, next, the spectrum time-series change calculating means 640 determines a time-series change in a spectrum of each frequency, and determines a spectrograph. Then, the distribution rate waveform calculating means 660 extracts three frequency components of 0.0017 Hz, 0.0035 Hz and 0.0053 Hz from the spectrograph that is a time-series change in the power spectrum, and sets a sum of the power spectrum values of the three components to 100, thereby determining a variation rate of each proportion as a distribution rate, as shown in FIG. 17C.

Figure 18:
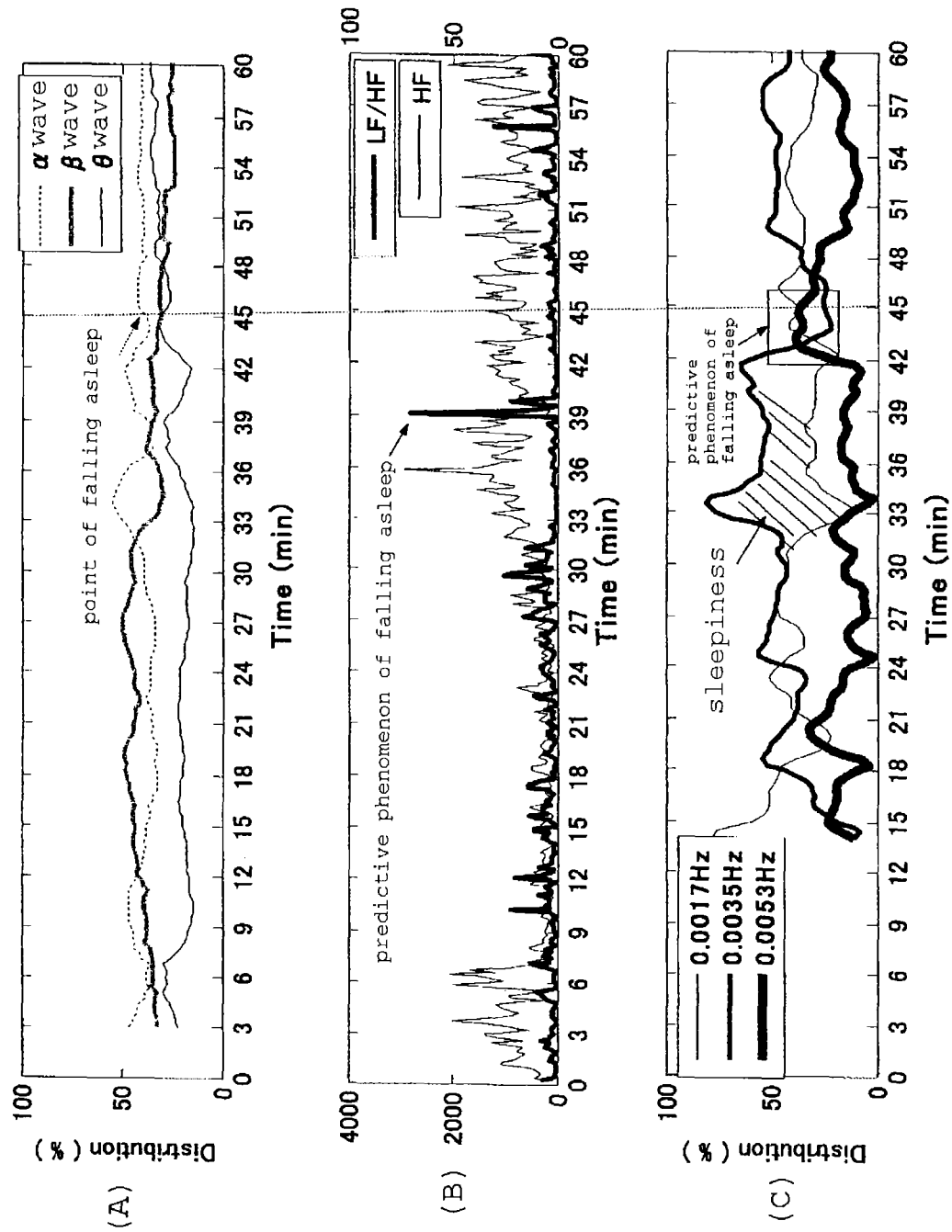
FIGS. 18A to C are diagrams showing an analysis result of the sleep introduction experiment applied to a human subject who is a man in his thirties.

FIG. 18 is an analysis result of the sleep introduction experiment applied to a human subject, who is a man in his thirties. FIG. 18A is a diagram showing time-series changes in distribution rates of a θ wave (4 to 7 Hz), an α wave (8 to 13 Hz), and a β wave (18 to 30 Hz) of the brain waves. FIG. 18B is a diagram showing emergence degrees of the sympathetic nervous and parasympathetic nervous which are determined by subjecting the fingertip plethysmogram to a wavelet analysis. FIG. 18C is a diagram showing a time-series changes in distribution rates of 0.0017 Hz, 0.0035 Hz and 0.0053 Hz which are determined from the time-series waveform in the above manner after a heart-part oscillation wave is measured and a frequency slope time-series waveform is determined by using the zero-crossing method (0x detection method).

Referring to FIG. 18A, the α wave is disturbed after 33 minutes pass since the experience starts; and after 34 minutes pass, the α wave exhibits the decline tendency and the θ wave is rapidly increased to over 20%. Accordingly, the sleepiness emerges at this time. At the time when 45 minutes pass, the α wave falls below 50% and the θ wave exceeds 20%; and afterward the waves hover stably. Therefore, it is determined that he fell asleep at the time when 45 minutes pass since the distribution rates of the brain waves change in time sequence. Referring to FIG. 18B, a state where the sympathetic nervous is dominant is shifted to a state where the parasympathetic nervous is dominant, at the time when 32 minutes pass since the experience starts, and a burst wave of the sympathetic nervous which indicates a prediction of falling asleep is generated at the time when 39 minutes pass. Thus, this exhibits a similar tendency to that of the determination using the brain waves.

Meanwhile, referring to FIG. 18C, at the time when 34 minutes pass since the experience starts, the distribution rate of 0.0053 Hz is minimized and the distribution rates of 0.0017 Hz and 0.0035 Hz become opposite in phase. In addition, it can be seen that 0.0053 Hz is rapidly increased in the vicinity of the time when 42 minutes pass. Comparing those with FIGS. 18A and B, it is said that the anti-phase of the distribution rates of 0.0017 Hz and 0.0035 Hz indicates a predictive phenomenon of falling asleep. In addition, as is clear from FIG. 18B, the temporal increase in the LF/HF (sympathetic nerve) is observed when the predictive phenomenon of falling asleep is generated. Thus, the rapid increase in 0.0053 Hz in FIG. 18C is considered to reflect the activity of the sympathetic nervous.

When the variations in the distribution rates of the brain waves in FIG. 18A are further compared to those of the three frequency components in the heart-part oscillation wave in FIG. 18C, 0.0017 Hz, 0.0035 Hz and 0.0053 Hz exhibit the same tendencies as those of θ, α and β waves, respectively, between 32 to 44 minutes during which the α and θ waves repeat a rapid change. By utilizing a one-dimensional template matching, an index (Mk) that indicates a matching degree between the variations in the distribution rates of the brain waves in FIG. 18A and the variations in the distribution rates of the three frequency components of the heart-part oscillation wave in FIG. 18C is determined from the following equation.

$$Mk = \Sigma(G(i) - T(j))^2 / N$$

Figure 19:
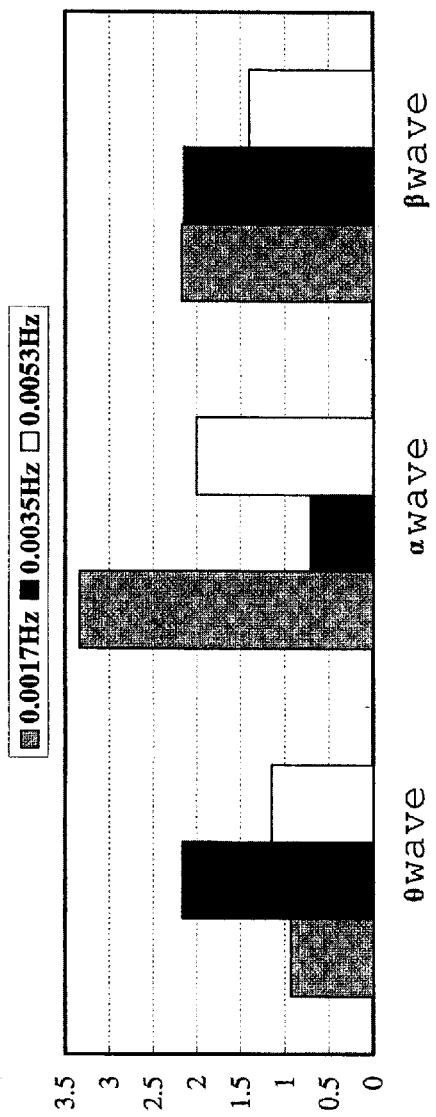
FIG. 19 is a diagram for explaining a matching degree of a distribution rate between a brain wave and a heart-part oscillation wave.

Note that G(i) is given a distribution rate of a heart-part oscillation wave which is comparison verification data, and T(i) is given a distribution rate of a brain wave which is a template waveform. The result is shown in FIG. 19. As the value of this index Mk is decreased, the matching degree is increased, and it can be seen from FIG. 19 that 0.0017 Hz, 0.0035 Hz and 0.0053 Hz are approximate to θ, α and β waves, respectively.

Furthermore, as for each of the 22 human subjects undergoing the sleep introduction experiment, the distribution rates of the brain waves were compared to those of the above three frequency components in the heart-part oscillation wave, and portions in which the increases in the θ and α waves of the brain waves and the increases in 0.0017 Hz and 0.0035 Hz of the heart-part oscillation wave appeared at the same time were checked. When the θ wave was increased, the increases in 0.0017 Hz appeared at 16 portions and the increases in 0.0035 Hz appeared at 7 portions. As a result, when the α wave was increased, the increases in 0.0017 Hz appeared at 5 portions and the increases in 0.0035 Hz appeared at 13 portions. Thus, the θ wave and 0.0017 Hz exhibit a high correlation, and the α wave and 0.0035 Hz exhibit a high correlation. Generally, it is considered that the α wave emerges during rest or in the relaxed state, and the fluctuation of 0.0035 Hz is related to the activity of the parasympathetic nervous. This can also be found from the fact that the distribution rate of 0.0035 Hz in FIG. 18C is high in a time zone in which the parasympathetic nervous is dominant in FIG. 18B.

Next, as for each of the human subjects for the representative example in the sleep introduction experiment, the waveforms indicating the distribution rates of the above three frequency components in the heart-part oscillation wave and states of the subjects were analyzed. Each of the three frequency components was calculated by both the zero-crossing method (0x detection method) and the peak detection method. Then, in the distribution rate waveforms obtained by at least one of the zero-crossing method (0x detection method) and the peak detection method, a time zone in which 0.0017 Hz and 0.0035 Hz were opposite in phase was compared to states of the subjects during this time zone. The result is shown in FIG. 20.

Referring to FIG. 20, a relatively large number of persons fell into a nap or fell asleep within the time zone in which 0.0017 Hz and 0.0035 Hz were opposite in phase.

During the anti-phase time zone, when 0.0017 Hz exhibited a higher distribution rate than 0.0035 Hz (APW(1)); when 0.0035 Hz exhibited a higher distribution rate than 0.0017 Hz (APW(2)); when time zones during which 0.0017 Hz exhibited a high distribution rate and during which 0.0035 Hz exhibited a high distribution rate are sequentially present (APW(3)); and when the anti-phase of 0.0017 Hz and 0.0035 Hz was generated and 0.0053 Hz was increased (APW(4)), it was checked whether the human subjects fell asleep later or not.

As shown in FIG. 20, as a result, APW(1), APW(2), APW(3) and APW(4) exhibit 55.6%, 66.7%, 50% and 72.2%, respectively. Accordingly, correlation data in which the waveform change patterns of the APW(1), APW(2), APW(3) and APW(4) were set to states of "weak sleepiness", "strong sleepiness", "resisting sleepiness" and "prediction of falling asleep", respectively, is stored in the storage unit. The determining means 670 determines a state of a human being by locating a waveform change pattern and by identifying one among the above waveform change patterns to which the located waveform change pattern corresponds.

Note that as shown in FIG. 20, it is possible to determine sleepiness and prediction of falling asleep, even when the three frequency components are calculated by any of zero-crossing method (0x detection method) and peak detection method, and although any of them can be used, which method is used for each individual person may be set in view of the difference in sensitivity among persons. Furthermore, both methods are always used, and the appearance of the anti-phase in both can also be determined to be the phenomena of sleepiness and prediction of falling asleep. However, in the case where the biological signal measuring means of the present invention is disposed in an automobile or the like and is used for anti-dozing sensing, the appearance of the anti-phase in either one may be determined to be sleepiness and prediction of falling asleep. This is considered to be very effective at preventing dozing.

FIG. 21 is a diagram showing a slope time-series waveform pattern in the awake state which is produced by the zero-crossing method, and shows a comparison between a waveform and psychological determination (being awakened or feeling light sleepiness).

In FIG. 22, results determined to be "awake" are denoted by "Awake", and results determined to be "dozing or sleepiness" or "falling asleep" are denoted by "Sleep" in the psychological determination (APW(+)) of FIG. 20, and results determined to be "awake" are denoted by "Awake", and results determined to be "light sleepiness" are denoted by "Sleep" in the psychological determination (APW(−)) of FIG. 21. Then, FIG. 22 shows a correlation therebetween. Consequently, $X^2$ (chi-square value)=30.98 and since it is larger than 3.841 that is a value of P=5% when the degree of freedom is 1, it is said that the statistical significance is present between the APW(−) and the APW(+).

Figures 23, 24:
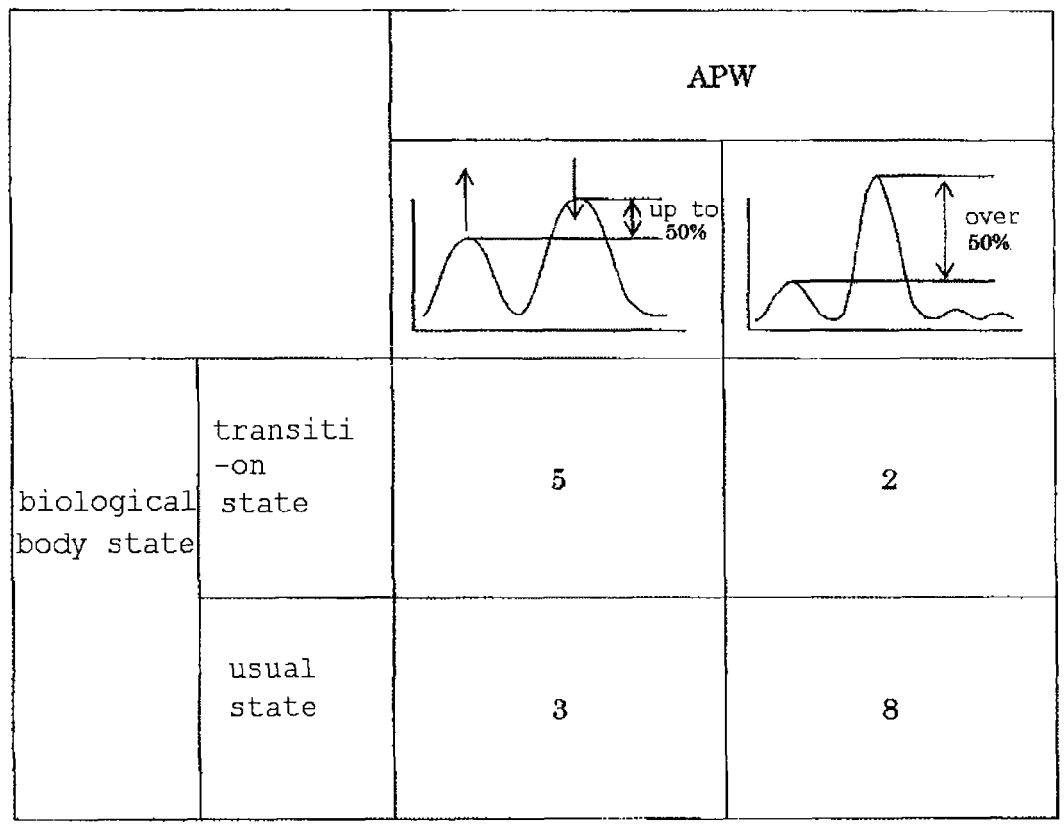
FIG. 23 is a diagram showing a correlation between results of FIGS. 20 and 21 and a state of a human being.
FIG. 24 is a diagram showing a method of making a determination from an original waveform of a heart-part oscillation wave (APW).

FIG. 23 is a summary of the number of examples in which the human subjects fell asleep and the number of examples in which the human subjects did not fall asleep in the APWs(1), (2), (3) and (4) in the case of the psychological determination (APW(+)) of FIG. 20, and the number of examples in which the subjects fell asleep and the number of examples in which the subjects did not fall asleep in the case of the psychological determination (APW(−)) of FIG. 21. Consequently, $X^2$ (chi-square value)=26.97 and since it is larger than 5.991 that is a value of P=5% when the degree of freedom is 2, it is said that the statistical significance is present among the APW(−), the APWs(1), (2) and (3), and the APW(4).

FIG. 24 shows a method of making a determination from an original waveform of a heart-part oscillation wave (APW). In more detail, a transition state (a state where sleepiness is generated and a state where the predictive phenomenon of falling asleep emerges) and a steady state (awake state) are determined on the basis of a height proportion of a power spectrum produced as a frequency analysis result for an original waveform of an APW. The transition state is defined as a state where a value obtained by dividing a peak value of f0 into a peak value of a frequency of ⅓f0 to ½f0 is equal to more than 50% when an average frequency of a heart rate fluctuation is denoted by f0. Consequently, it is also possible to determine the steady state and the transition state even from the original waveform of the APW although this determination contains some variation.

Figure 25:
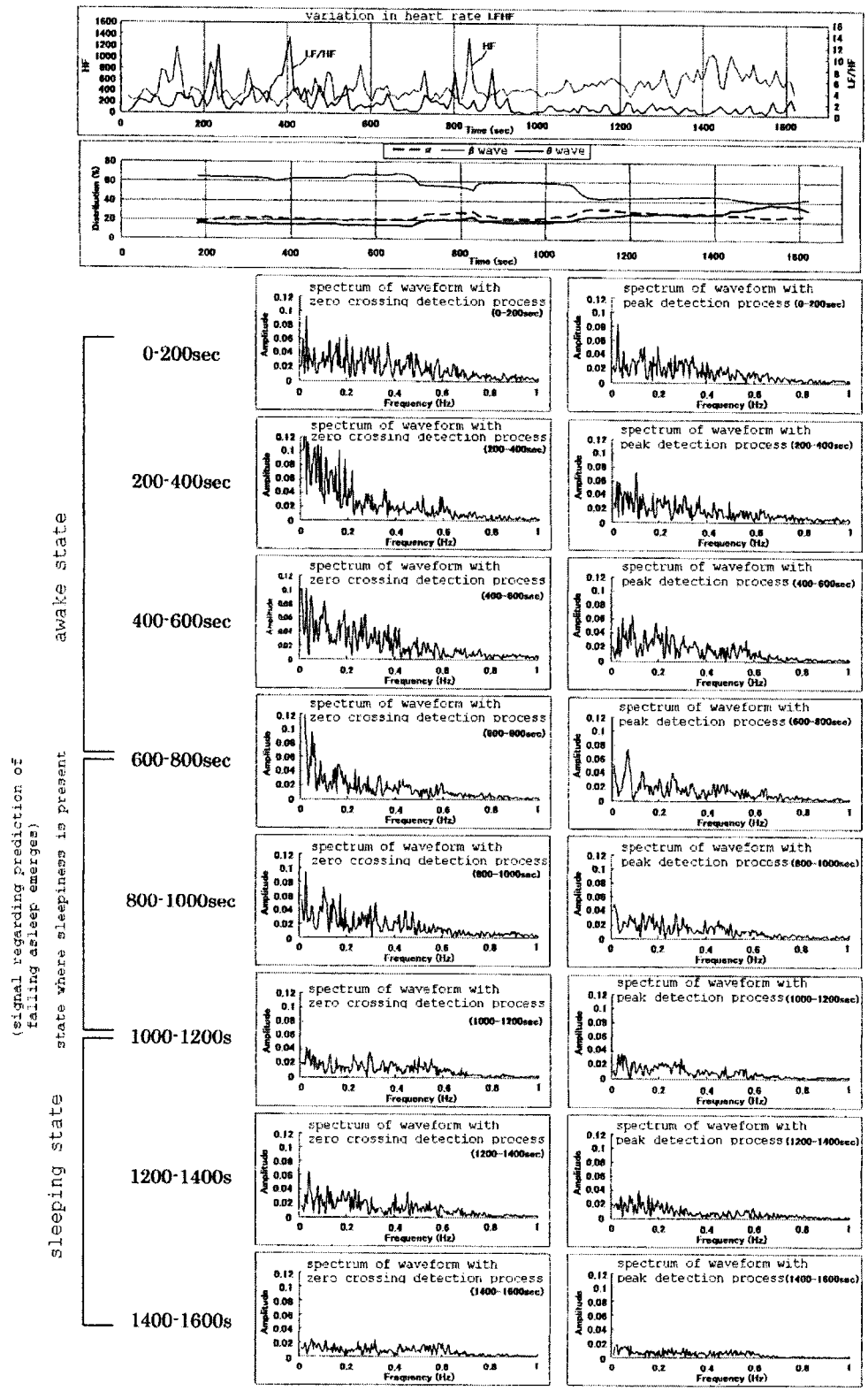
FIG. 25 shows a comparison between each of waveforms of the APW which are produced by using the zero crossing and peak detection methods and each of a brain wave and an activity of an automatic nerve.

FIG. 25 shows a comparison between each of waveforms of the APW which are produced by using the zero crossing and peak detection methods and each of a brain wave and an activity of an automatic nerve. FIGS. 26A and B show results of: analyzing frequencies of waveforms of the APW in FIG. 25 which are produced by the zero crossing and peak detection methods; using a power spectrum in the sleeping state as a reference; and determining states where the analyzed waveform exceeds 30% and 100% of the reference, as a phenomenon of sleepiness and prediction of falling asleep and a steady (awake) state, respectively. Consequently, it is believed that it is possible to determine the steady state and the transition state from these waveforms, and in particular it is possible to make a more precise determination when a waveform produced by the zero crossing detection method is used.

INDUSTRIAL APPLICABILITY

The present invention is applicable to a case of estimating a passenger's state, such as a sleepiness state or the like, by disposing the biological signal measuring means in a seat of a vehicle, including an automobile, as well as a case of estimating a state by disposing the biological signal measuring means in a chair located in a house, an office chair, or the like. Moreover, the present invention is also applicable to a case of estimating a state of a human being by: disposing the biological signal measuring means in furniture, such as a bed or the like; and capturing and analyzing a back aortic oscillation with the above biological signal measuring device. This makes it possible to easily grasp a health condition of a sleeping person (in particular, a person who is sick or receives care) through a screen displayed on a monitor of display means.

REFERENCE SIGNS LIST 1 biological signal measuring means
10 three-dimensional knitted material
15 three-dimensional knitted material supporting member
15a through-hole for arrangement
16 film
21, 22 plate-shaped foam body
30 vibration sensor
100 seat
110 seatback frame
120 skin
60 biological body state estimation device
610 first frequency calculating means
620 second frequency calculating means
630 first frequency slope time-series analysis calculating means
640 second frequency slope time-series analysis calculating means
650 spectrum time-series change calculating means
660 distribution rate waveform calculating means
670 determining means

The invention claimed is:

1. A biological body state estimation device which acquires a biological signal from an upper body of a human being and estimates a state of a human being by using the biological signal, comprising:
  circuitry configured to:
  calculate frequency to determine a time-series waveform of a frequency from a time-series waveform of a biological signal acquired by a biological signal measuring mechanism;
  calculate frequency slope time-series analysis to subject the time-series waveform of the frequency of the biological signal to movement calculation to determine a slope of the frequency at each predetermined time window set with a predetermined overlap time, and to output a time-series change in the slope of the frequency acquired at each time window as a frequency slope time-series waveform;
  calculate spectrum time-series change to analyze a frequency of the frequency slope time-series waveform, and to determine a time-series change in a power spectrum;
  calculate distribution rate waveform to extract frequency components corresponding to a preset functional adjustment signal, fatigue reception signal and activity adjustment signal from the time-series change in the power spectrum, for to calculate proportions of three frequency components in time sequence when a sum of power spectrums of the three frequency components is set to 100, and to determine the proportions as distribution rate waveforms; and
  locate a waveform change pattern of the three frequency components in the distribution rate waveforms, and determine a state of a human being by comparing the located waveform change pattern with correlative data between a waveform change pattern and a state of a human being which the correlative data is stored in a storage unit in advance.

2. The biological body state estimation device according to claim 1, the circuitry further configured to:
  calculate first frequency to pinpoint a zero-crossing point in the time-series waveform of the biological signal obtained by the biological signal measuring mechanism, and to determine the time-series waveform of the frequency of the biological signal by using the zero-crossing point, the zero-crossing point being a point at which a positive of the time-series waveform is switched to a negative,
  calculate first frequency slope time-series analysis to subject the time-series waveform of the frequency of the biological signal to the movement calculation to determine the slope of the frequency at each predetermined time window set with the predetermined overlap time, and to output the time-series change in the slope of the frequency acquired at each time window as the frequency slope time-series waveform, and
  analyze the frequency of the frequency slope time-series waveform, and determine the time-series change in the power spectrum.

3. The biological body state determination device according to claim 1, the circuitry further configured to:
  calculate second frequency to determine a maximum value of the time-series waveform of the biological signal obtained from the biological signal measuring mechanism by smoothing and differentiating the time-series waveform, and determining the time-series waveform of the frequency of the biological signal by using the maximum value,
  calculate second frequency slope time-series analysis to subject the time-series waveform of the frequency of the biological signal to the movement calculation to determine the slope of the frequency at each predetermined time window set with the predetermined overlap time, and to output the time-series change in the slope of the frequency acquired at each time window as the frequency slope time-series waveform, and
  analyze the frequency of the frequency slope time-series waveform, and determine the time-series change in the power spectrum.

4. The biological body state determination device according to claim 1, circuitry configured to:
  determine a time zone in which the functional adjustment signal and the fatigue reception signal are opposite in phase to be a period during which a sleepiness-related phenomenon emerges, as the waveform change pattern of the distribution rate waveform.

5. The biological body state determination device according to claim 4, circuitry configured to:
determine a time zone in which the functional adjustment signal and the fatigue reception signal are opposite in phase and the distribution rate of the activity adjustment signal is equal to or higher than a predetermined distribution rate to be a period during which a predictive phenomenon of falling asleep emerges, as the waveform change pattern of the distribution rate waveform.

6. The biological body state determination device according to claim 1, wherein
a frequency of the functional adjustment signal is 0.0017 Hz, a frequency of the fatigue reception signal is 0.0035 Hz, and a frequency of the activity adjustment signal is 0.0053 Hz.

7. A non-transitory computer readable medium to be set in a biological body state estimation device which acquires a biological signal from an upper body of a human being and estimates a state of a human being by using the biological signal, causing a computer to perform a process comprising:
determining a time-series waveform of a frequency from a time-series waveform of a biological signal acquired by a biological signal measuring mechanism;
subjecting the time-series waveform of the frequency of the biological signal to movement calculation for determining a slope of the frequency at each predetermined time window set with a predetermined overlap time, and outputting a time-series change in the slope of the frequency acquired at each time window as a frequency slope time-series waveform;
analyzing a frequency of the frequency slope time-series waveform, and determining a time-series change in a power spectrum;
extracting frequency components corresponding to a preset functional adjustment signal, fatigue reception signal and activity adjustment signal from the time-series change in the power spectrum calculating proportions of the three frequency components in time sequence when a sum of power spectrums of the three frequency components is set to 100, and determining the proportions as distribution rate waveforms; and
locating a waveform change pattern of the three frequency components in the distribution rate waveforms, and determining a state of a human being by comparing the located waveform change pattern with correlative data between a waveform change pattern and a state of a human being which the correlative data is stored in a storage unit in advance.

8. The non-transitory computer readable medium according to claim 7, the process further comprising:
pinpointing a zero-crossing point in the time-series waveform of the biological signal obtained by the biological signal measuring mechanism, and determining the time-series waveform of the frequency of the biological signal by using the zero-crossing point, the zero-crossing point being a point at which a positive of the time-series waveform is switched to a negative,
subjecting the time-series waveform of the frequency of the biological signal to the movement calculation to determine the slope of the frequency at each predetermined time window set with the predetermined overlap time, and outputting the time-series change in the slope of the frequency acquired at each time window as the frequency slope time-series waveform, and
analyzing the frequency of the frequency slope time-series waveform, and analyzing the time-series change in the power spectrum.

9. The non-transitory computer readable medium according to claim 7, the process further comprising:
determining a maximum value of the time-series waveform of the biological signal obtained from the biological signal measuring mechanism by smoothing and differentiating the time-series waveform, and determining the time-series waveform of the frequency of the biological signal by using the maximum value,
subjecting the time-series waveform of the frequency of the biological signal to the movement calculation to determine the slope of the frequency at each predetermined time window set with the predetermined overlap time, and outputting the time-series change in the slope of the frequency acquired at each time window as the frequency slope time-series waveform, and
analyzing the frequency of the frequency slope time-series waveform, and determining the time-series change in the power spectrum.

10. The non-transitory computer readable medium according to claim 8, wherein
a time zone in which the functional adjustment signal and the fatigue reception signal are opposite in phase is determined to be a period during which a sleepiness-related phenomenon emerges, as the waveform change pattern of the distribution rate waveform.

11. The non-transitory computer readable medium according to claim 10, wherein
a time zone in which the functional adjustment signal and the fatigue reception signal are opposite in phase and the distribution rate of the activity adjustment signal is equal to or higher than a predetermined distribution rate is determined to be a period during which a predictive phenomenon of falling asleep emerges, as the waveform change pattern of the distribution rate waveform.

12. The non-transitory computer readable medium according to claim 7, wherein
a frequency of the functional adjustment signal is 0.0017 Hz, a frequency of the fatigue reception signal is 0.0035 Hz, and a frequency of the activity adjustment signal is 0.0053 Hz.

* * * * *